United States Patent [19]

Iwaki et al.

[11] Patent Number: 5,188,762
[45] Date of Patent: Feb. 23, 1993

[54] MESOMORPHIC COMPOUND, LIQUID CRYSTAL COMPOSITION, LIQUID CRYSTAL DEVICE, DISPLAY APPARATUS AND DISPLAY METHOD

[75] Inventors: Takashi Iwaki, Machida; Takao Takiguchi, Tokyo; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 702,320

[22] Filed: May 20, 1991

[30] Foreign Application Priority Data

May 23, 1990 [JP] Japan .................... 2-134674

[51] Int. Cl.5 .................. C09K 19/32; G02F 1/13; C07F 7/08
[52] U.S. Cl. ...................... 252/299.62; 252/299.01; 252/299.61; 252/299.63; 252/299.66; 252/299.67; 359/103; 359/104; 544/229; 544/242; 544/298; 544/335; 556/415; 556/424; 556/438; 556/447; 560/59; 560/61; 560/62; 560/64; 560/65; 560/73; 560/76; 560/102
[58] Field of Search ........... 252/299.1, 299.61, 299.62, 252/299.63, 299.66, 299.67; 359/103, 104; 544/229, 242, 298, 315, 335; 556/415, 424, 436, 437, 438, 445, 447, 449; 560/8, 59, 61, 62, 64, 65, 73, 76, 80, 85, 102

[56] References Cited

U.S. PATENT DOCUMENTS

| | | | |
|---|---|---|---|
| 4,316,041 | 2/1982 | Totten et al. ............... | 252/299.62 |
| 4,367,924 | 1/1983 | Clark et al. ................. | 350/334 |
| 4,774,028 | 9/1988 | Imai et al. .................. | 252/299.01 |
| 5,106,530 | 4/1992 | Hass et al. .................. | 252/299.6 |

FOREIGN PATENT DOCUMENTS

| | | |
|---|---|---|
| 0355008 | 8/1990 | European Pat. Off. |
| 3827600 | 2/1990 | Fed. Rep. of Germany |
| 56-107216 | 8/1981 | Japan |

OTHER PUBLICATIONS

Schadt et al., "Applied Physics Letters," vol. 18, No. 4, pp. 127–128 (1971).

*Primary Examiner*—Richard D. Lovering
*Assistant Examiner*—Shean C. Wu
*Attorney, Agent, or Firm*—Fitzpatrick, Cella, Harper & Scinto

[57] ABSTRACT

A mesomorphic compound represented by the following formula (I):

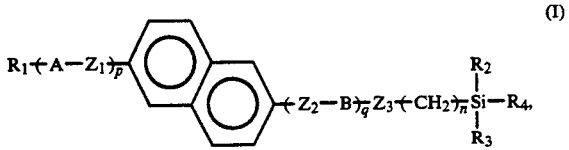

wherein $R_1$ denotes a linear or branched alkyl group having 2–16 carbon atoms capable of including one or two non-neighboring methylene groups which can be replaced with

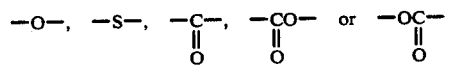

and capable of including fluorine substituted for hydrogen; A denotes —$A_1$— or —$A_1$—$A_2$— and B denotes —$B_1$— or —$B_1$—$B_2$— wherein $A_1$, $A_2$, $B_1$ and $B_2$ respectively denote (Abstract continued on next page.)

-continued

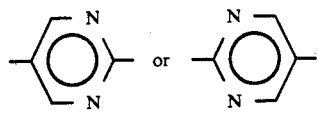

wherein $Y_1$ and $Y_2$ respectively denote H, F, Cl, Br, $-CH_3$, $-CN$ or $-CF_3$; $Z_1$ and $Z_2$ respectively denote

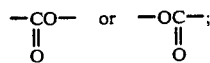

$Z_3$ denotes

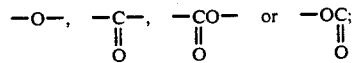

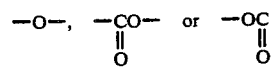

$R_2$, $R_3$ and $R_4$ respectively denote a linear or branched alkyl group having 1-16 carbon atoms including a methylene group which can be replaced with $$-O-,\ -\underset{\underset{O}{\|}}{C}O-\ \text{or}\ -O\underset{\underset{O}{\|}}{C}$$

with proviso that it is not adjacent to the silicon atom; p and q are respectively 0 or 1 with proviso that p+q is 0 or 1; and n is an integer of 1-12. The mesomorphic compound is effective for providing a ferroelectric liquid crystal composition showing an improved low-temperature operation characteristic and a decreased temperature-dependence of response speed.

36 Claims, 4 Drawing Sheets

MESOMORPHIC COMPOUND, LIQUID CRYSTAL COMPOSITION, LIQUID CRYSTAL DEVICE, DISPLAY APPARATUS AND DISPLAY METHOD

FIELD OF THE INVENTION AND RELATED ART

The present invention relates to a novel mesomorphic compound, a liquid crystal composition, a liquid crystal device, a display apparatus and a display method, and more particularly to a novel mesomorphic compound and a liquid crystal composition with improved responsiveness to an electric field, a liquid crystal device using the liquid crystal composition for use in a display device, a liquid crystal-optical shutter, etc., a display apparatus using the device, and a display method using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed and a smaller temperature-dependence of the response speed, a display apparatus using the device, and a display method using the composition and device.

According to the present invention, there is provided a mesomorphic compound represented by the following formula (I):

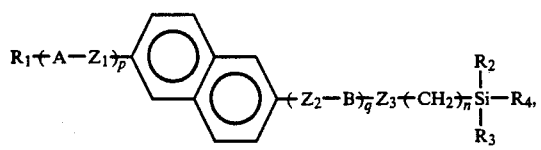
(I)

wherein $R_1$ denotes a linear or branched alkyl group having 2-16 carbon atoms capable of including one or two non-neighboring methylene groups which can be replaced with

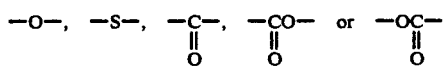

and capable of including fluorine substituted for hydrogen; A denotes $-A_1-$ or $-A_1-A_2-$ and B denotes $-B_1-$ or $-B_1-B_2-$ wherein $A_1$, $A_2$, $B_1$ and $B_2$ respectively denote

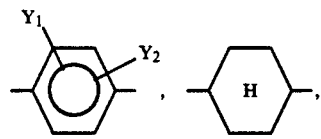

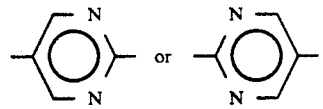

wherein $Y_1$ and $Y_2$ respectively denote H, F, Cl, Br, $-CH_3$, $-CN$ or $-CF_3$; $Z_1$ and $Z_2$ respectively denote

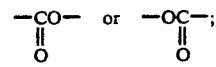

$Z_3$ denotes

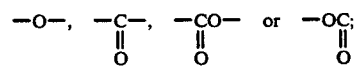

$R_2$, $R_3$ and $R_4$ respectively denote a linear or branched alkyl group having 1-16 carbon atoms including a methylene group which can be replaced with

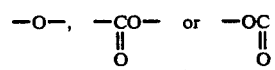

with proviso that it is not adjacent to the silicon atom; p and q are respectively 0 or 1 with proviso that p+q is 0 or 1; and n is an integer of 1-12.

According to the present invention, there is further provided a liquid crystal composition containing at least one species of the mesomorphic compound as described above.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by using voltage application means to effect display.

We found that a compound including a naphthalene ring in its skeleton and a trialkyl silylakyl group as an end group had a low melting point and a wide temperature range of a mesomorphic phase. We also found that a liquid crystal device using a liquid crystal composition containing at least one compound described above showed improved characteristics such as a good alignment characteristic, high-speed responsiveness and a decreased temperature-dependence of response speed, thus showing good display characteristics.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
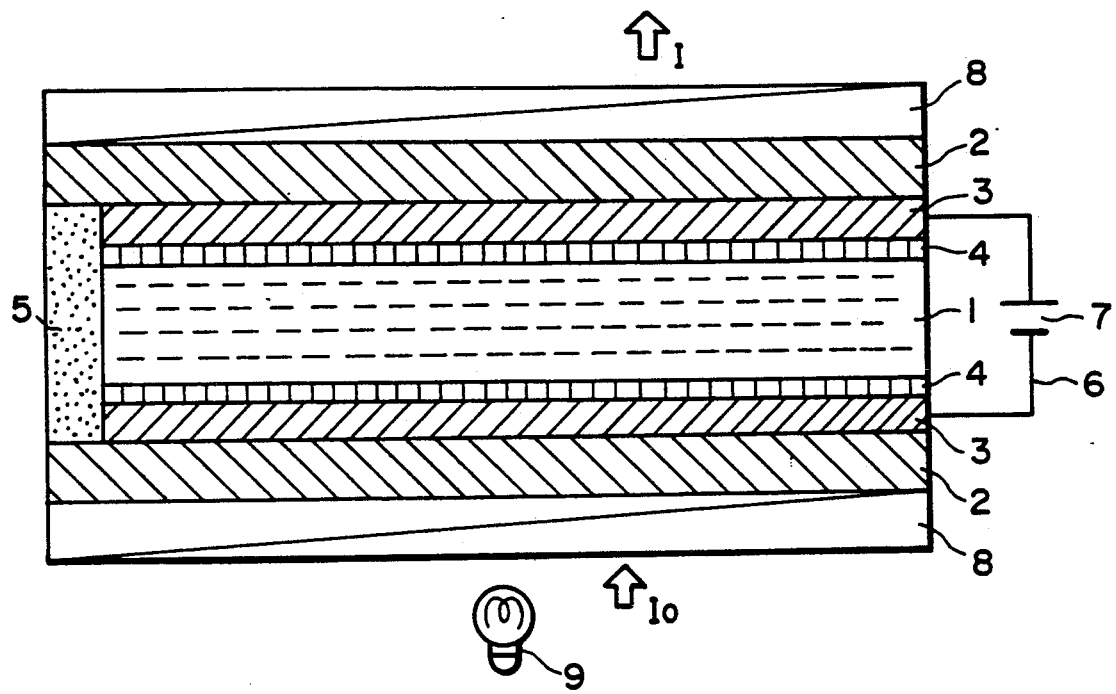
FIG. 1 is a schematic sectional view of a liquid crystal display device using a liquid crystal composition assuming a chiral smectic phase.

In the formula (I) as described above, preferred examples of $R_1$ may includes an alkyl group, an alkoxy group, an alkanoyloxy group and an alkoxycarbonyl group.

Preferred examples of $A_1$, $A_2$, $B_1$ and $B_2$ may respectively include

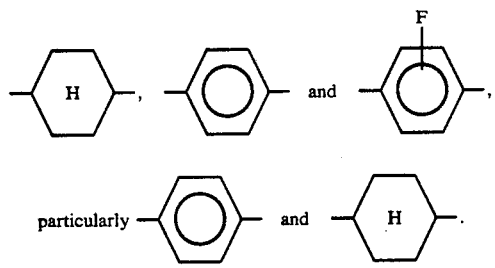

Further, $R_2$, $R_3$ and $R_4$ each may preferably include an alkyl group having 1-12 carbon atoms, particularly a linear alkyl group having 1-8 carbon atom.

The compounds represented by the general formula (I) may be synthesized through the following reaction schemes.

(Case where p = q = 0)

When $Z_3$ = O

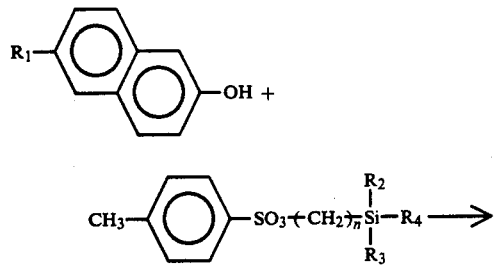

When $Z_3$ = COO

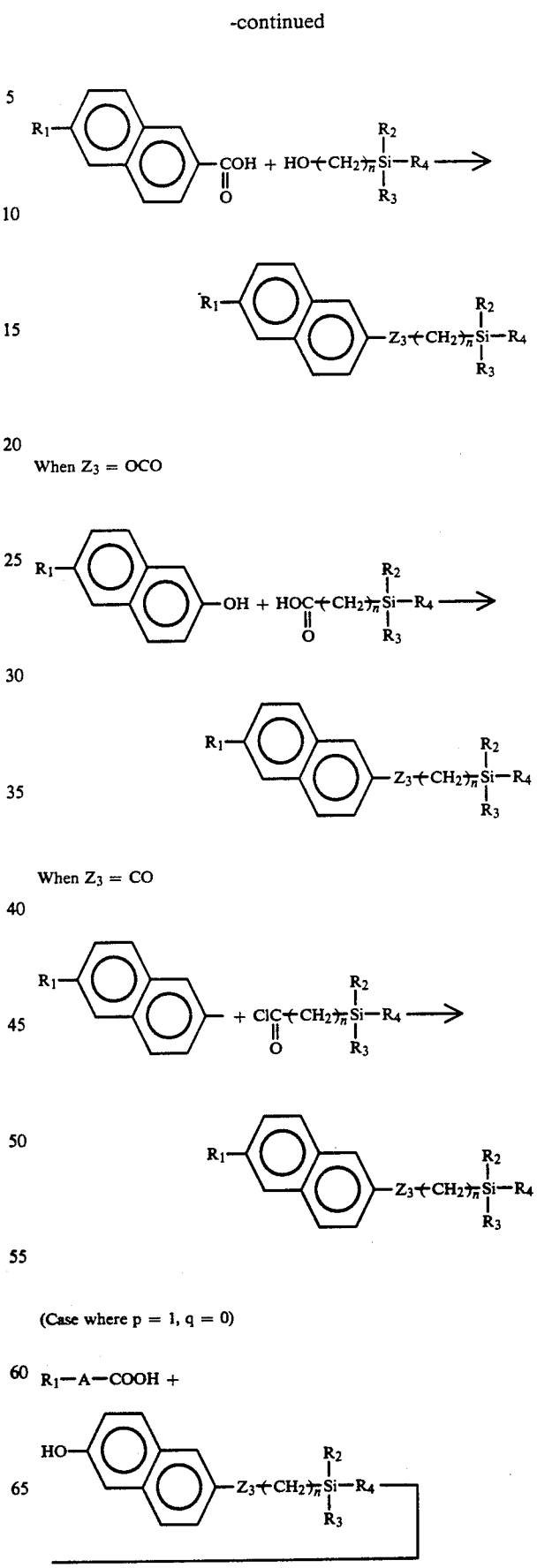

(Case where p = 1, q = 0)

$R_1-A-COOH +$

-continued
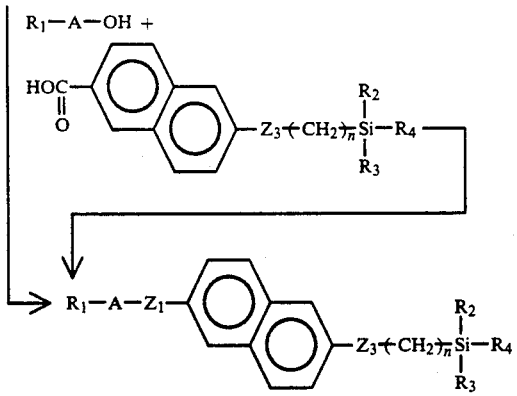
(Case where p = 0 and q = 1)
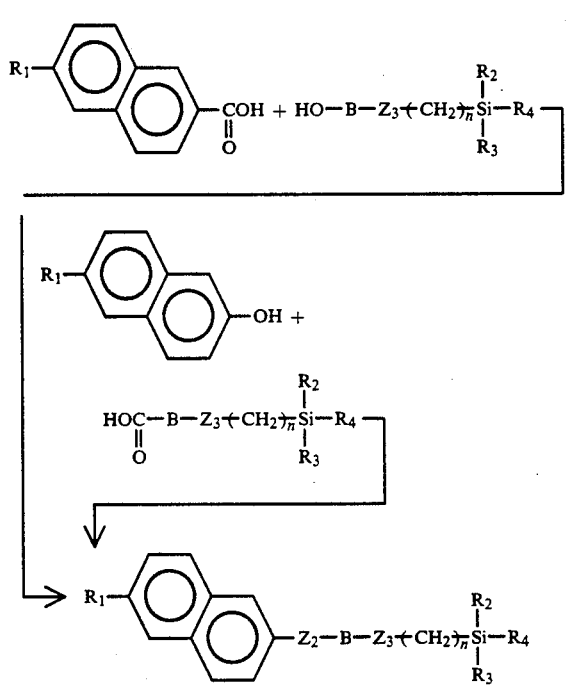
It is possible to finally introduce the
structure to the compounds of the formula (I).
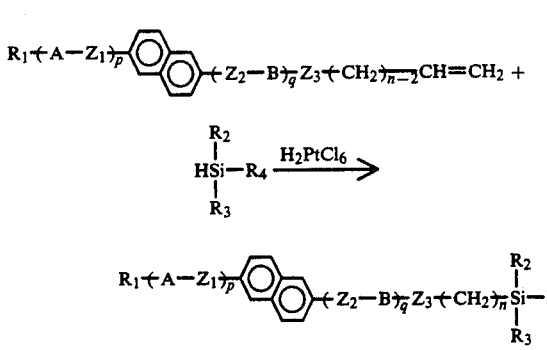
In the above $R_1$, $R_2$, $R_3$, $R_4$, A, B, $Z_1$, $Z_2$, $Z_3$, p, q and n are the same as defined above.
Specific examples of the mesomorphic compounds represented by the above-mentioned general formula (I) may include those shown by the following structural formulas.
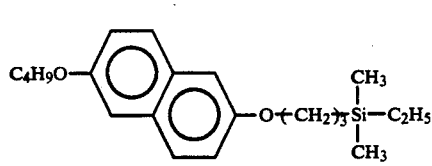
(I-1)
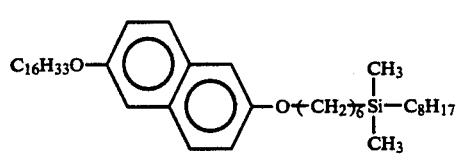
(I-2)
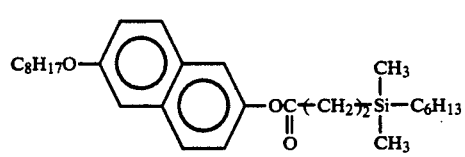
(I-3)

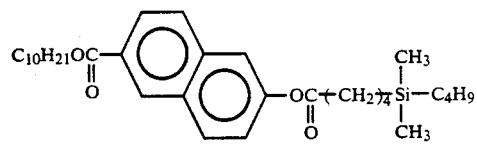 (I-4)
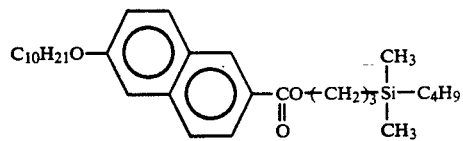 (I-5)
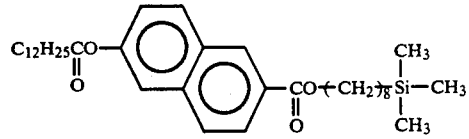 (I-6)
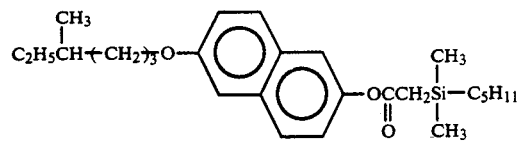 (I-7)
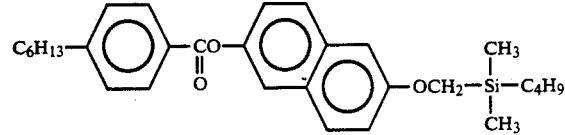 (I-8)
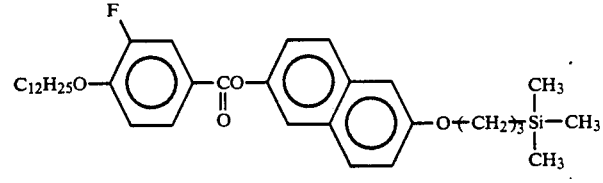 (I-9)
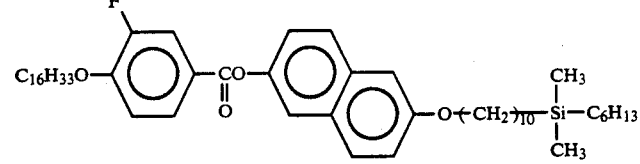 (I-10)
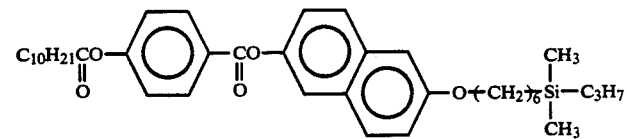 (I-11)
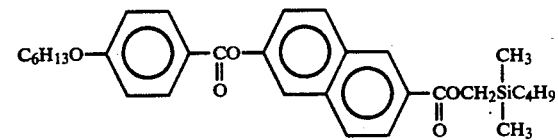 (I-12)
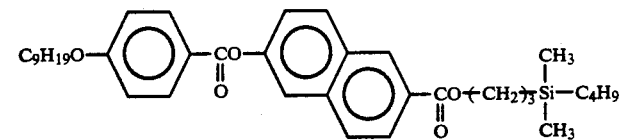 (I-13)

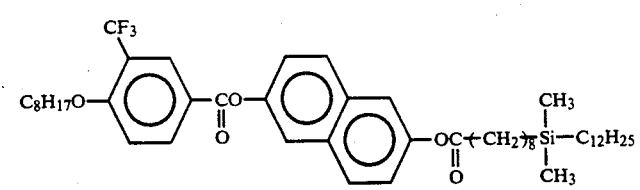
(I-14)
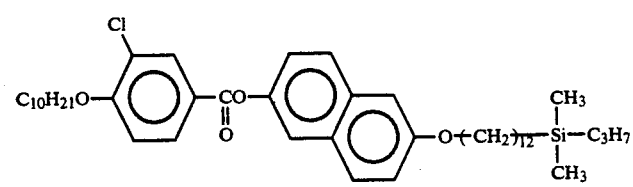
(I-15)
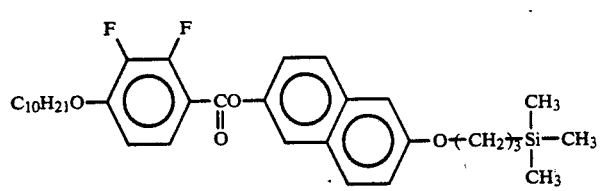
(I-16)
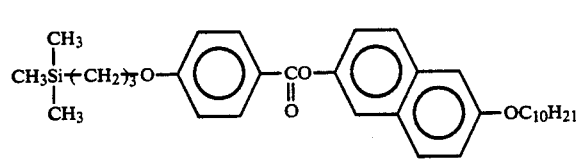
(I-17)
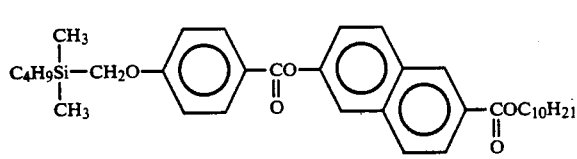
(I-18)
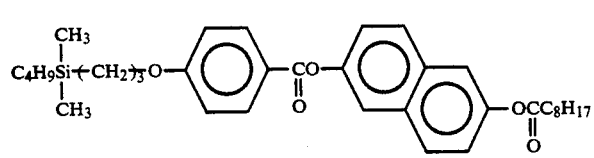
(I-19)
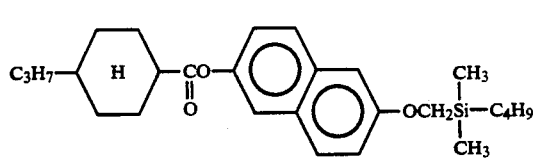
(I-20)
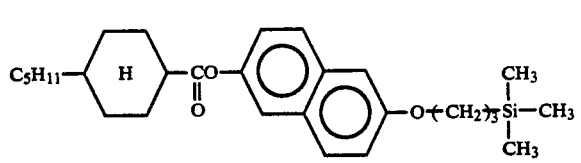
(I-21)
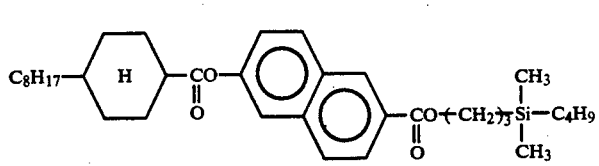
(I-22)

-continued
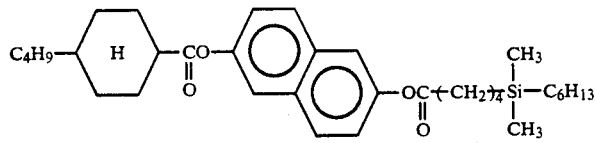
(I-23)
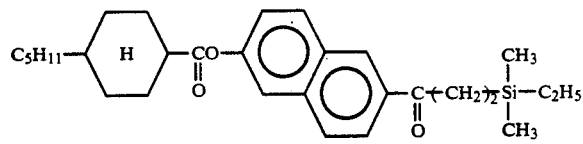
(I-24)
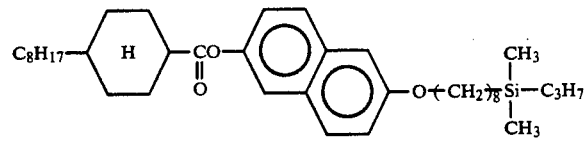
(I-25)
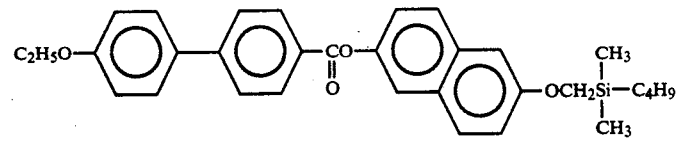
(I-26)
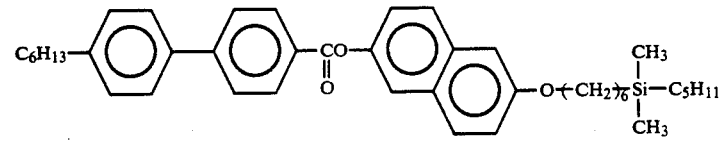
(I-27)
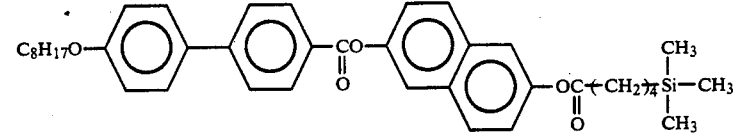
(I-28)
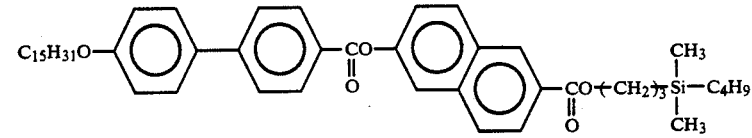
(I-29)
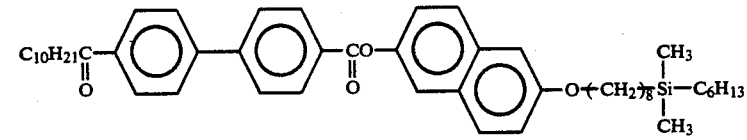
(I-30)
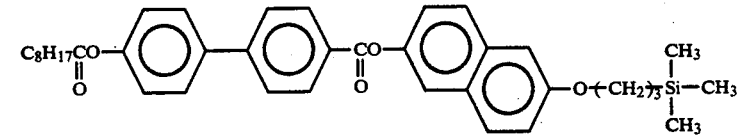
(I-31)
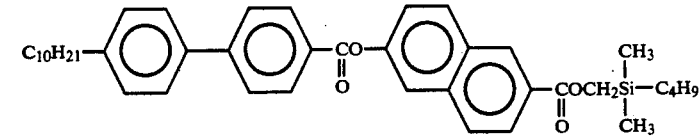
(I-32)

-continued
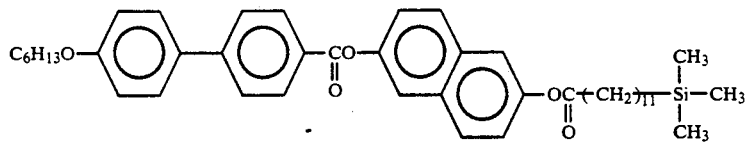 (I-33)
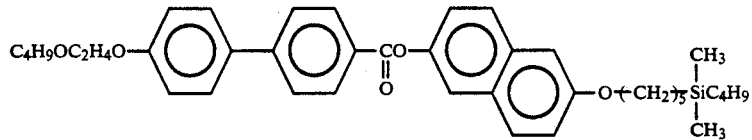 (I-34)
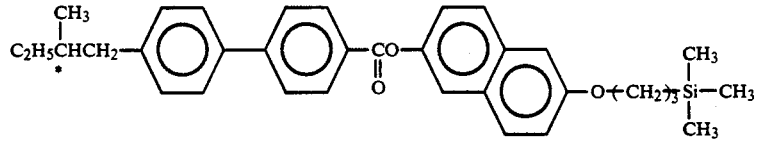 (I-35)
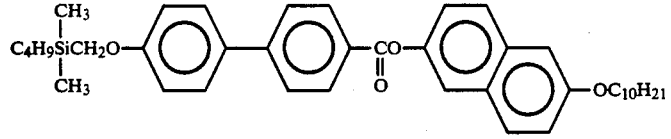 (I-36)
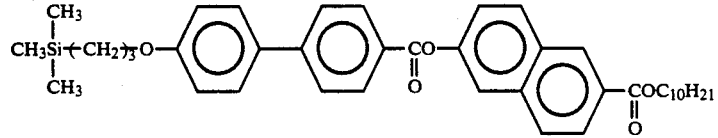 (I-37)
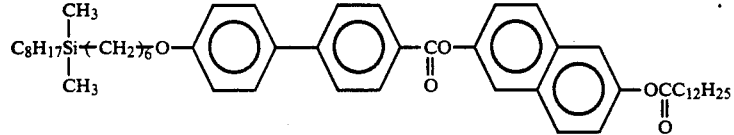 (I-38)
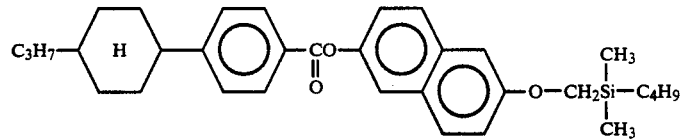 (I-39)
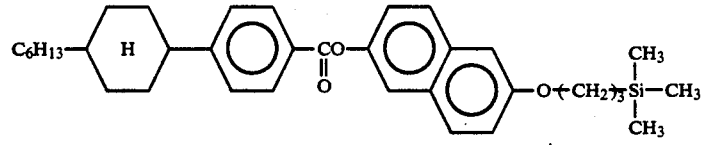 (I-40)
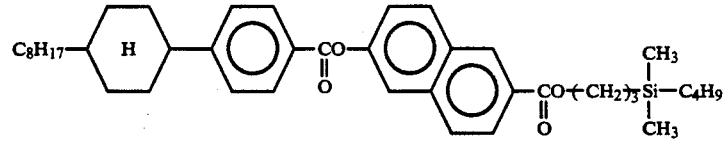 (I-41)
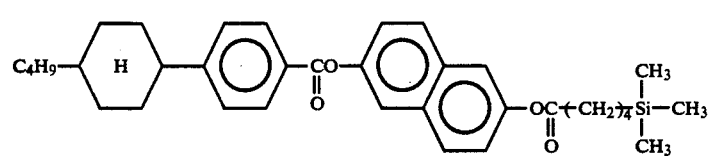 (I-42)

-continued
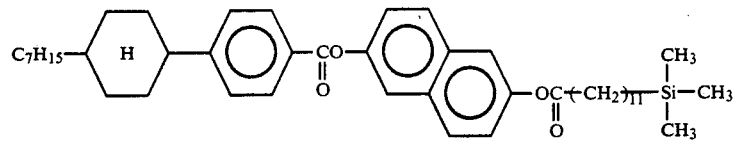 (I-43)
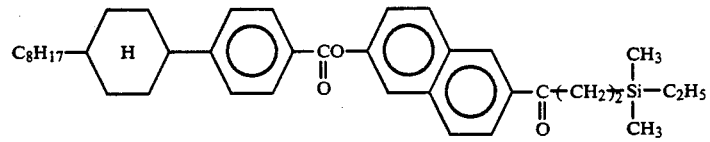 (I-44)
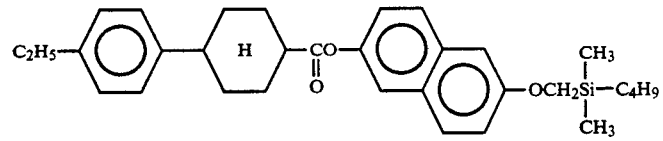 (I-45)
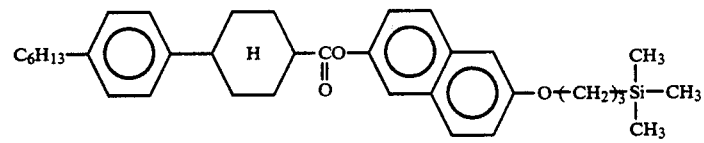 (I-46)
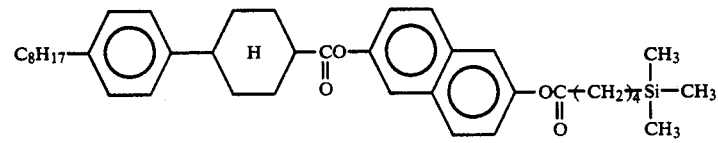 (I-47)
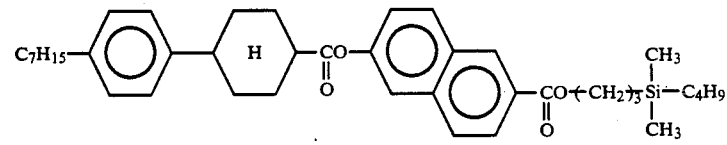 (I-48)
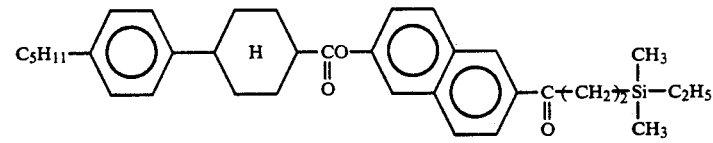 (I-49)
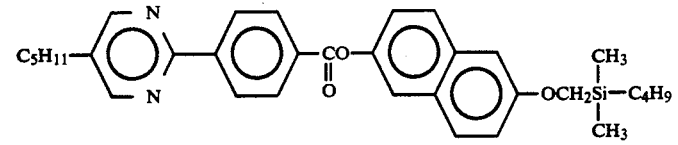 (I-50)
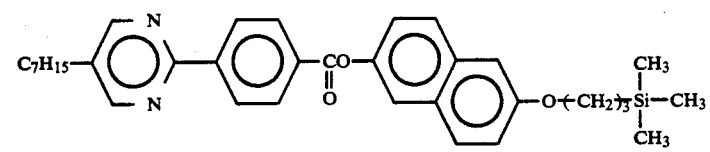 (I-51)
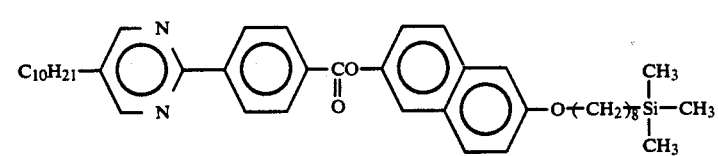 (I-52)

-continued
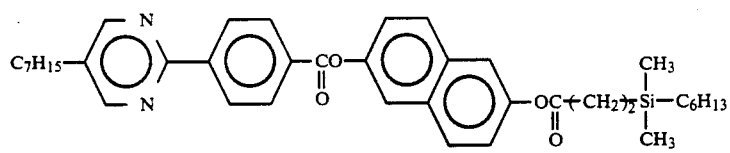 (I-53)
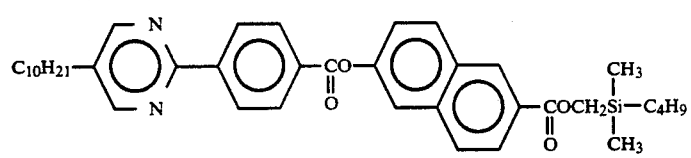 (I-54)
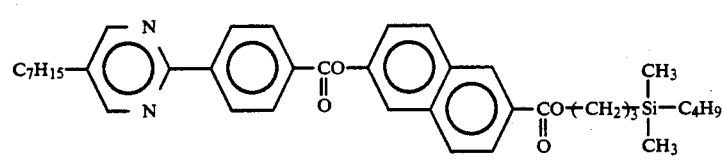 (I-55)
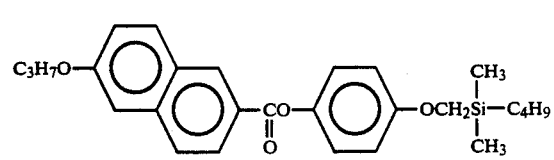 (I-56)
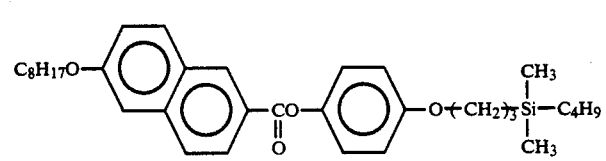 (I-57)
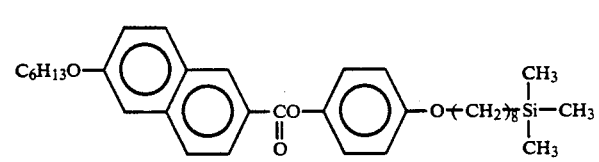 (I-58)
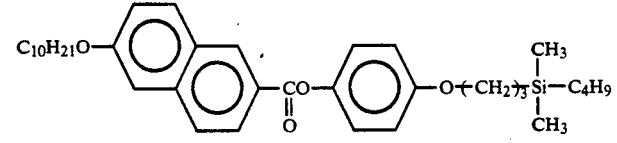 (I-59)
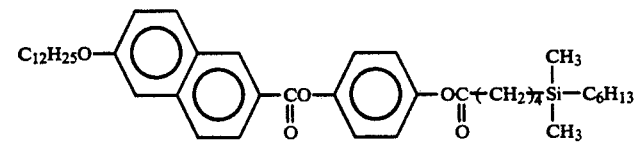 (I-60)
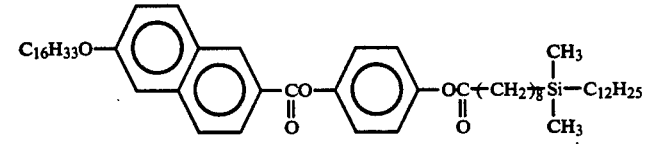 (I-61)
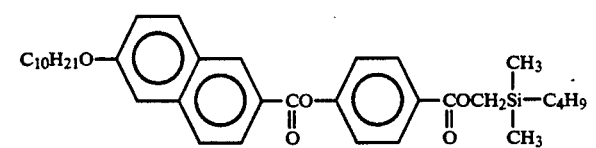 (I-62)

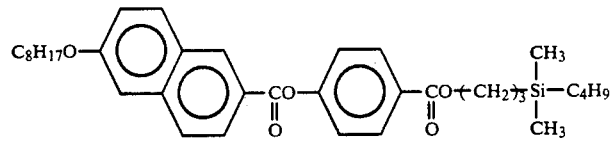
(I-63)
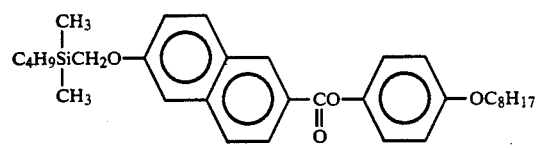
(I-64)
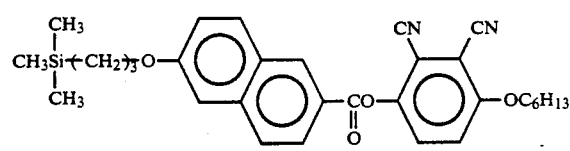
(I-65)
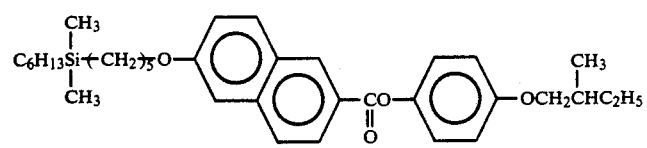
(I-66)
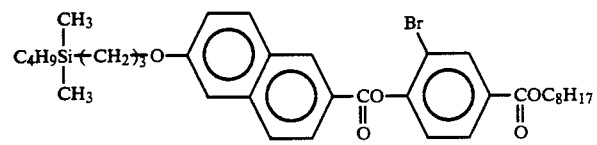
(I-67)
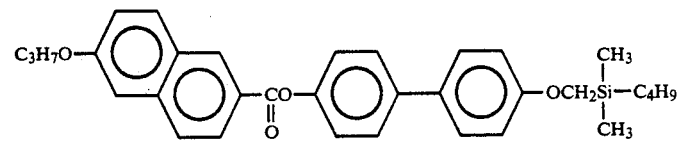
(I-68)
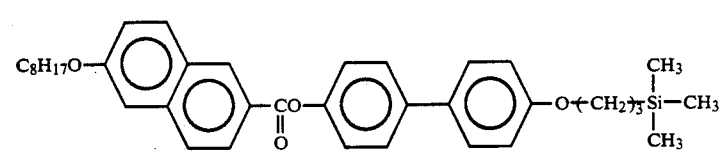
(I-69)
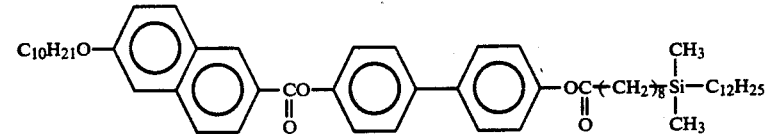
(I-70)
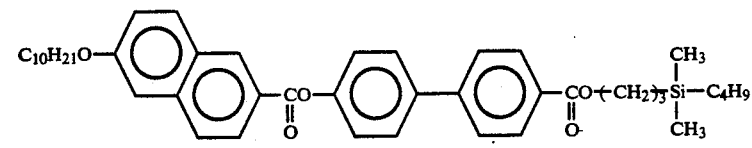
(I-71)
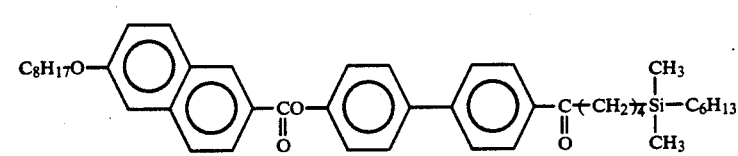
(I-72)

-continued
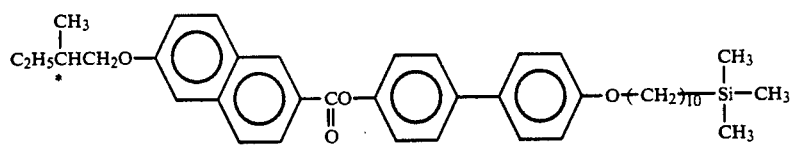
(I-73)
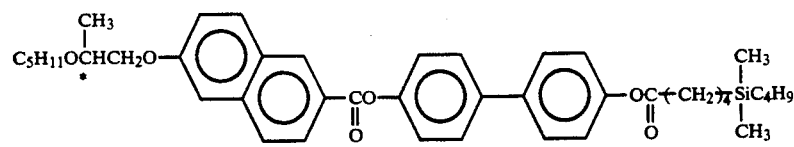
(I-74)
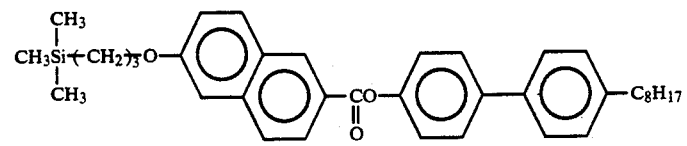
(I-75)
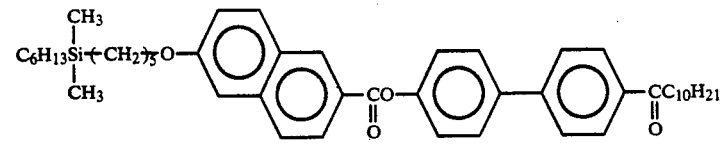
(I-76)
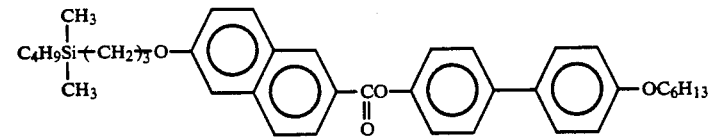
(I-77)
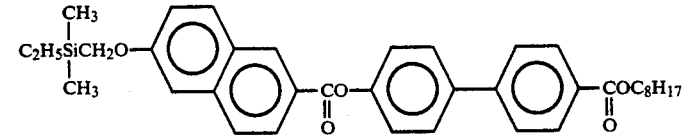
(I-78)
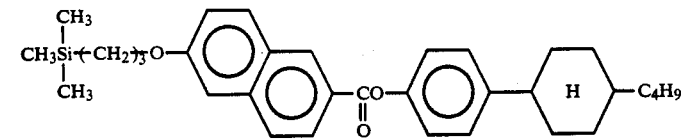
(I-79)
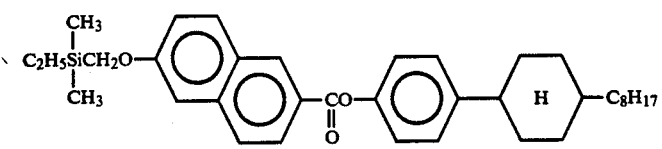
(I-80)
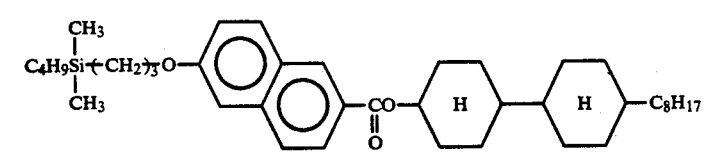
(I-81)
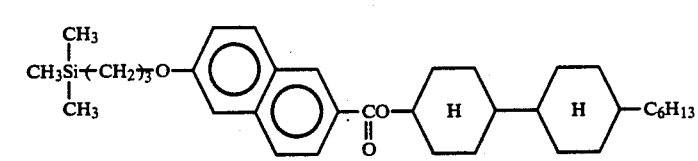
(I-82)

-continued
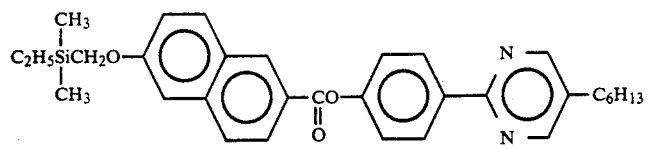 (I-83)
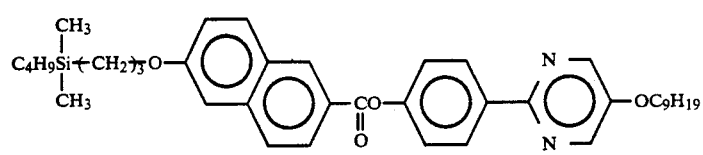 (I-84)
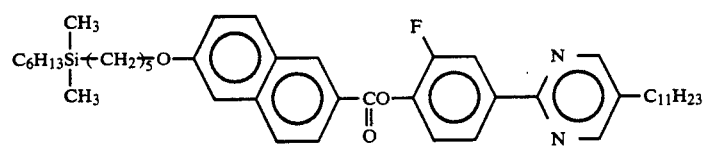 (I-85)
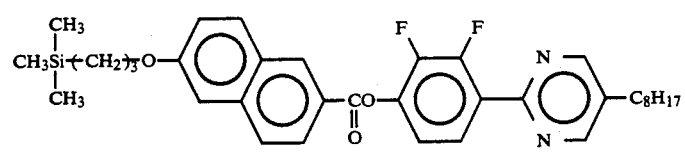 (I-86)
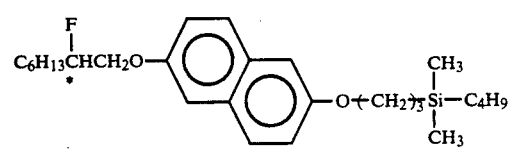 (I-87)
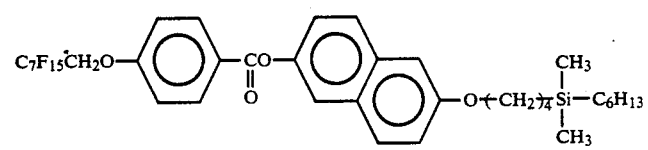 (I-88)
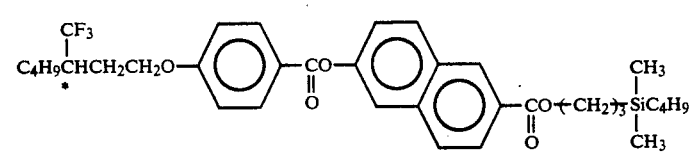 (I-89)
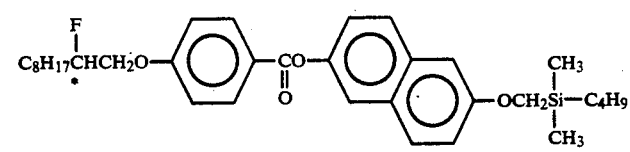 (I-90)
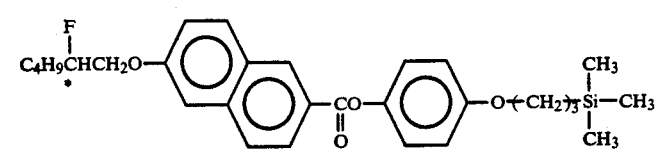 (I-91)
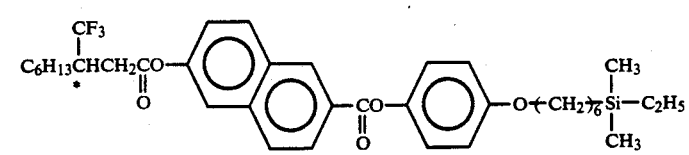 (I-92)

-continued
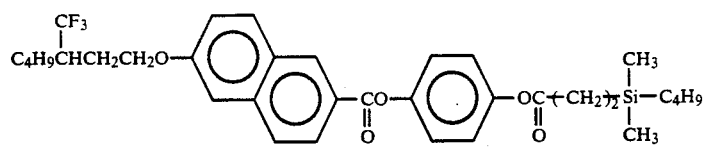 (I-93)
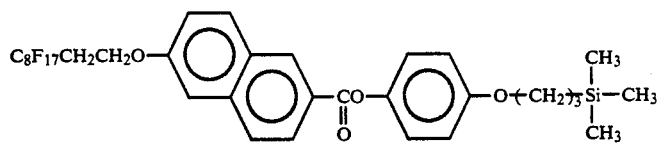 (I-94)
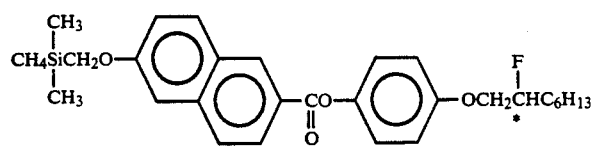 (I-95)
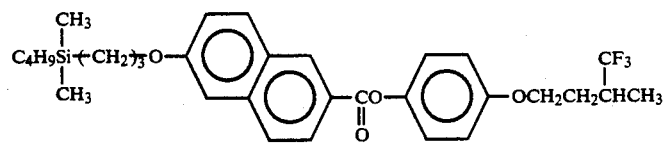 (I-96)
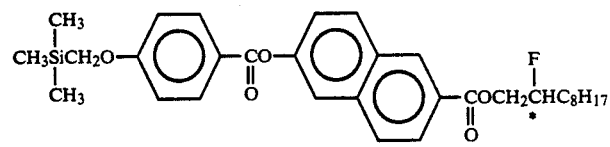 (I-97)
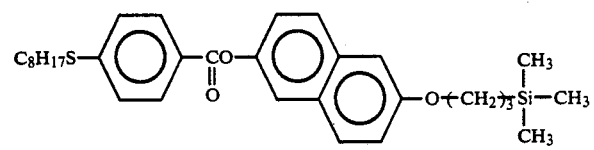 (I-98)
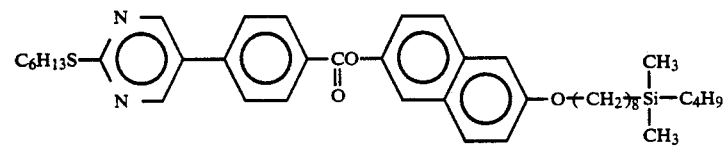 (I-99)
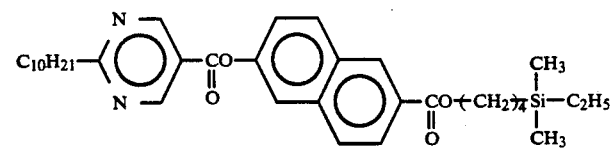 (I-100)
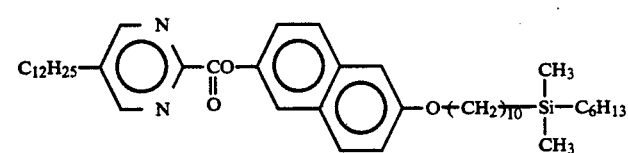 (I-101)
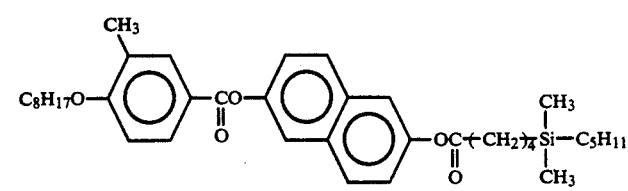 (I-102)

-continued
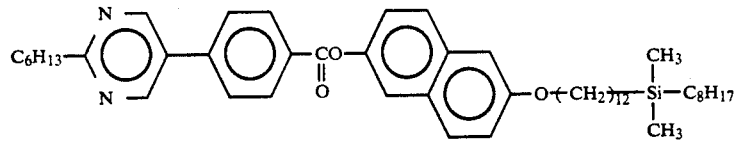 (I-103)
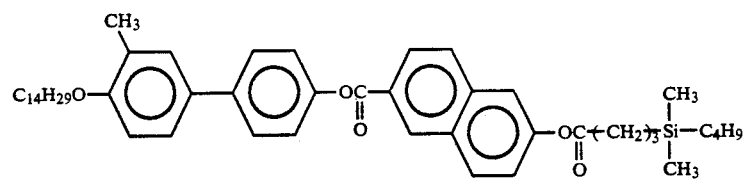 (I-104)
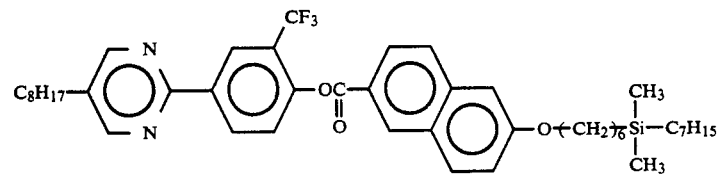 (I-105)
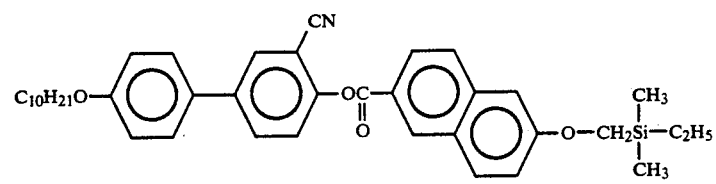 (I-106)
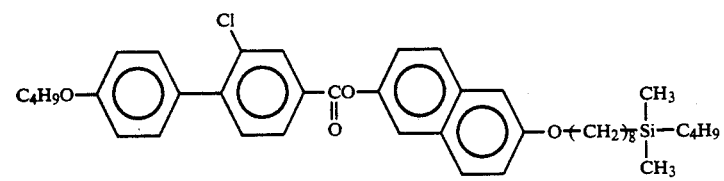 (I-107)
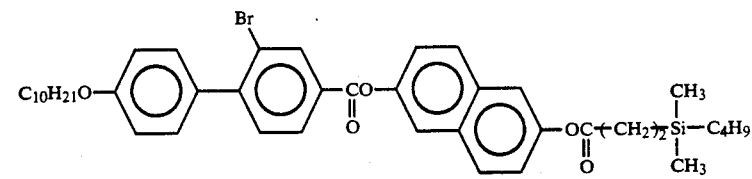 (I-108)
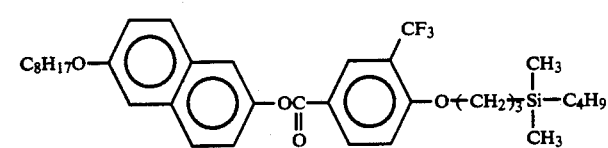 (I-109)
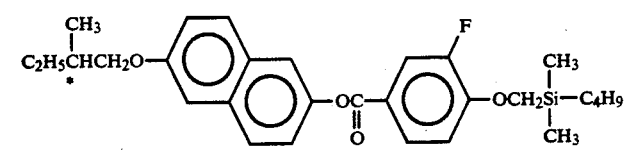 (I-110)
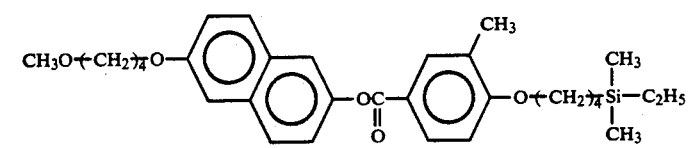 (I-111)

(I-112)
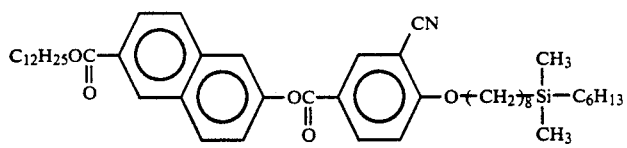
(I-113)
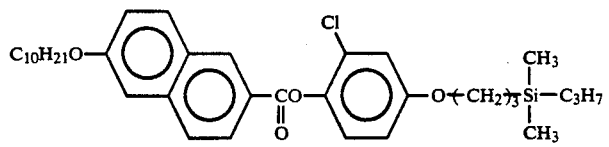
(I-114)
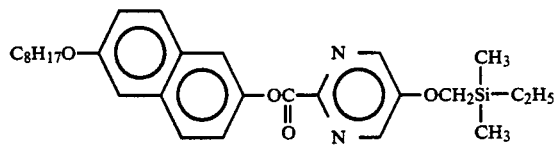
(I-115)
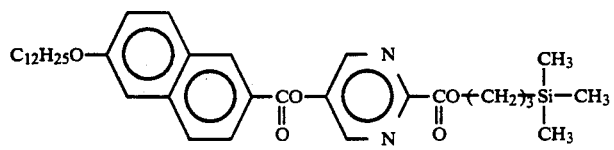
(I-116)
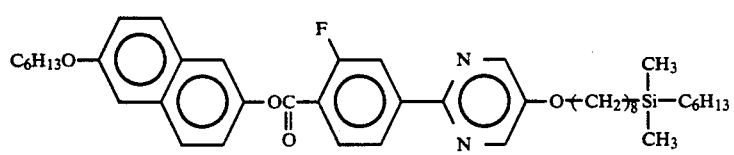
(I-117)
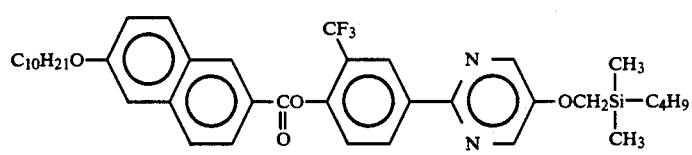
(I-118)
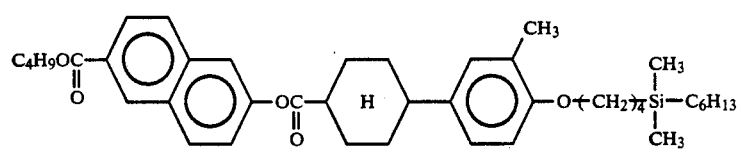
(I-119)
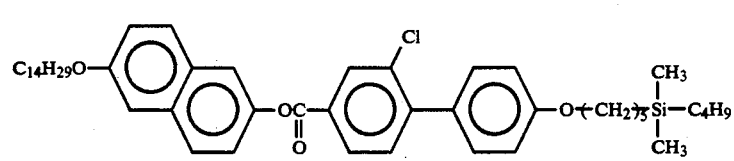
(I-120)
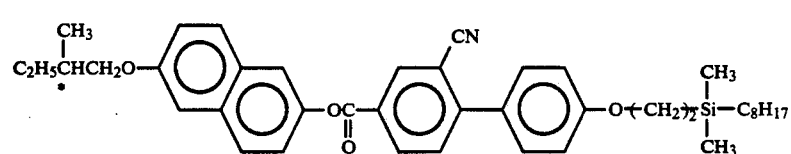
(I-121)
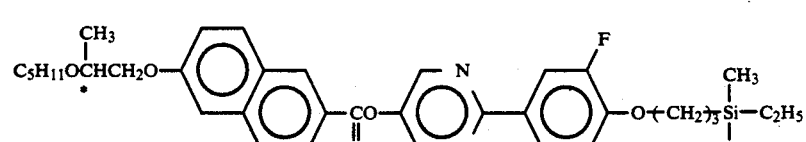

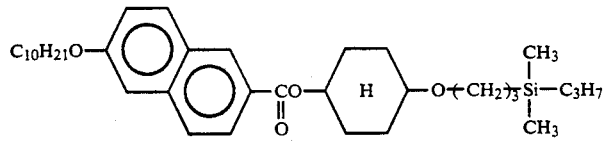
(I-122)

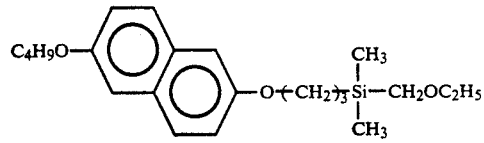
(I-123)

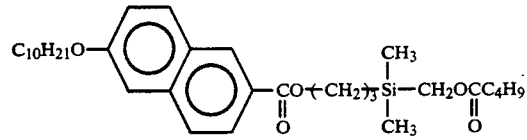
(I-124)

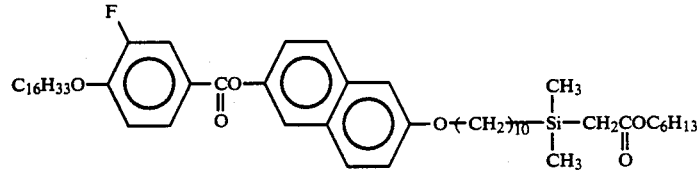
(I-125)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XI).

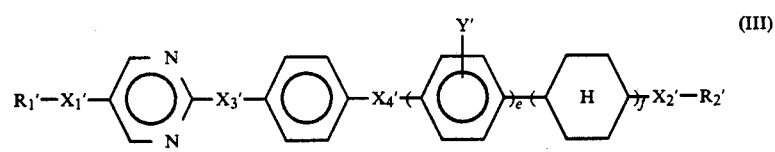
(III)

wherein e denotes 0 or 1 and f denotes 0 or 1 with proviso that e+f=0 or 1; Y' denotes H, halogen, $CH_3$ or $CF_3$; $X_1'$ and $X_2'$ respectively denote a single bond, $$-\underset{\underset{O}{\|}}{C}O-,\ -O\underset{\underset{O}{\|}}{C}-,\ -O-\ \text{or}\ -O\underset{\underset{O}{\|}}{C}O-;$$

and $X_3'$ and $X_4'$ respectively denote a single bond, $$-\underset{\underset{O}{\|}}{C}O-,\ -O\underset{\underset{O}{\|}}{C}-,\ -OCH_2-\ \text{or}\ -CH_2O-.$$

In the formula (III), preferred compounds thereof may include those represented by the following formulas (IIIa) to (IIId):

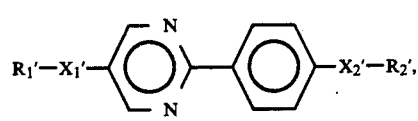
(IIIa)

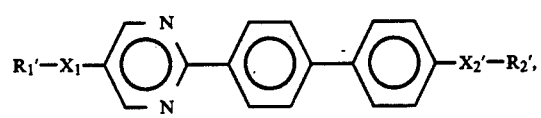
(IIIb)

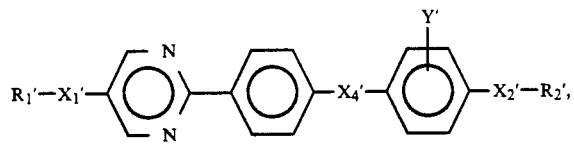
(IIIc)

and

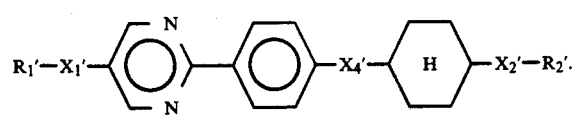
(IIId)

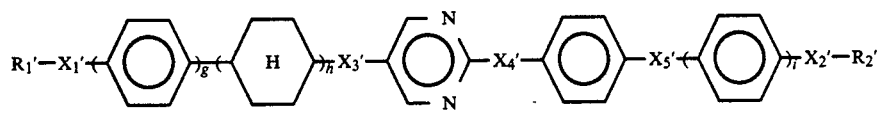
(IV)

wherein g and h respectively denote 0 or 1 with proviso that g+h=1; i denotes 0 or 1; $X_1'$ and $X_2'$ respectively denote a single bond,

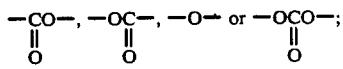

and $X_3'$, $X_4'$ and $X_5'$ respectively denote a single bond,

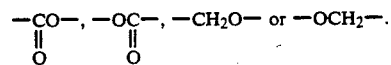

In the formula (IV), preferred compounds thereof may include those represented by the following formulas (IVa) to (IVc):

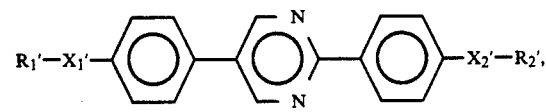
(IVa)

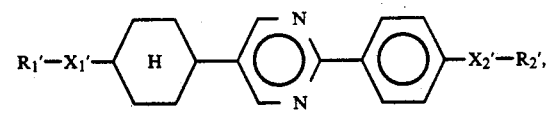
(IVb)

and

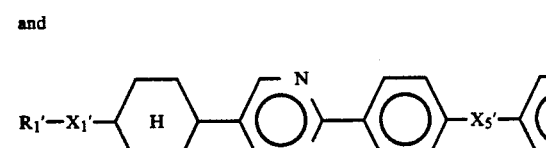
(IVc)

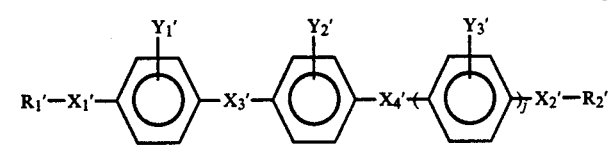
(V)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond,

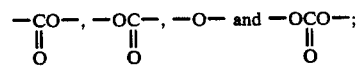

and $X_3'$ and $X_4'$ respectively denote a single bond,

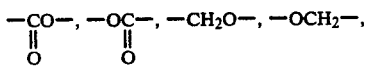

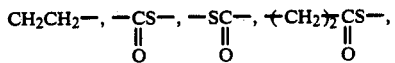

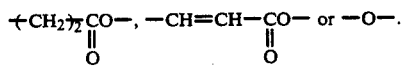

In the formula (V), preferred compounds thereof may include those represented by the following formulas (Va) and (Vb):

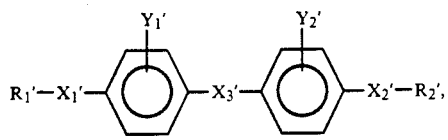 (Va)

and

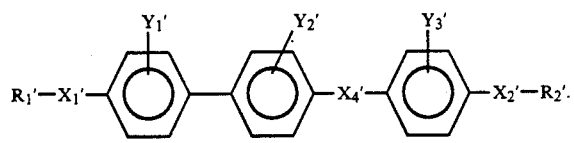 (Vb)

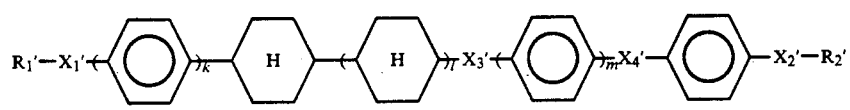 (VI)

wherein k, l and m respectively denote 0 or 1 with proviso that k+l+m=0, 1 or 2; $X_1'$ and $X_2'$ respectively denote a single bond,

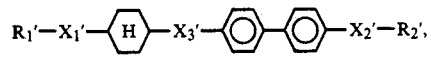

and $X_3'$ and $X_4'$ respectively denote a single bond,

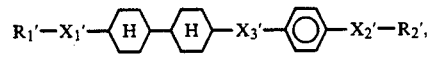

In the formula (VI), preferred compounds thereof may include those represented by the following formulas (VIa) to (VIf):

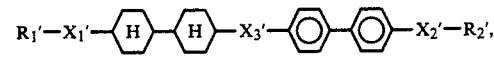 (VIa)

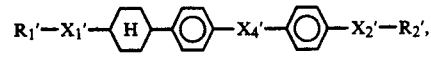 (VIb)

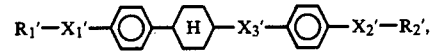 (VIc)

(VId)

(VIe)

and

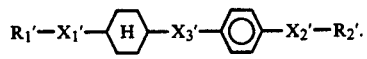 (VIf)

Herein, $R_1'$ and $R_2'$ respectively denote a linear or branched alkyl group having 1-8 carbon atoms capable of including one or two or more non-neighboring methylene groups which can be replaced with -CH halogen- and capable of further including one or two or more non-neighboring methylene groups other than those directly connected to $X_1'$ or $X_2'$ which can be replaced with at least one species of

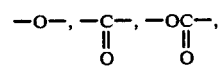

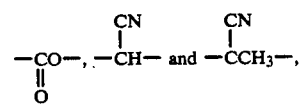

with proviso that $R_1'$ and $R_2'$ respectively do not connect to a ring structure by a single bond when $R_1'$ and $R_2'$ respectively denote a halogenated alkyl group containing one methylene group replaced with -CH halogen-.

Further, preferred examples of $R_1'$ and $R_2'$ may respectively include those represented by the following groups (i) to (vii):

i) a linear alkyl group having 1-15 carbon atoms;

ii) $-(CH_2)_p-CH(CH_3)-C_qH_{2q+1}$ wherein p denotes an integer of 0-5 and q denotes an integer of 1-11 (optically active or inactive);

iii) $-(CH_2)_r-CH(CH_3)-(CH_2)_s-OC_tH_{2t+1}$ wherein r denotes an integer of 0-6, s denotes 0 or 1, and t denotes an integer of 1-14 (optically active or inactive);

iv) $-(CH_2)_u-CH(F)-C_yH_{2y+1}$ wherein u denotes 0 or 1 and y denotes an integer of 1-16;

v) $-CH(CH_3)COC_wH_{2w+1}$ (with C=O)

wherein w denotes an integer of 1-15 (optically active or inactive);

vi) 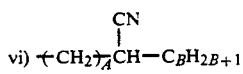

wherein A denotes an integer of 0–2 and B denotes an integer of 1–15 (optically active or inactive); and vii) 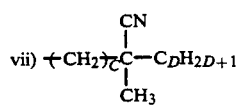

wherein C denotes an integer of 0–2 and D denotes an integer of 1–15 (optically active or inactive).

In the above-mentioned formula (III), more preferred compounds thereof may include those represented by the formulas (IIIaa) to (IIIdc):

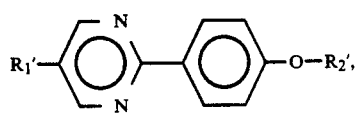 (IIIaa)

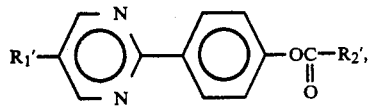 (IIIab)

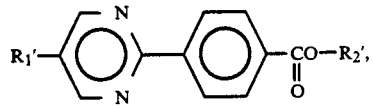 (IIIac)

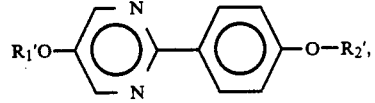 (IIIad)

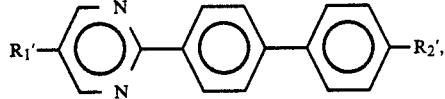 (IIIba)

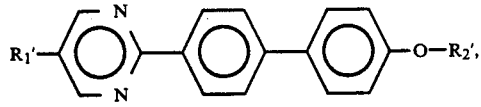 (IIIbb)

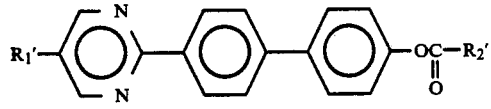 (IIIbc)

 (IIIbd)

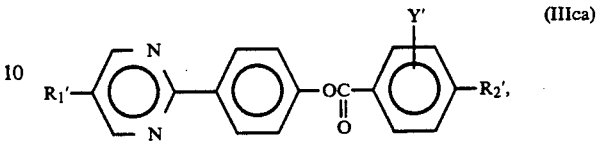 (IIIca)

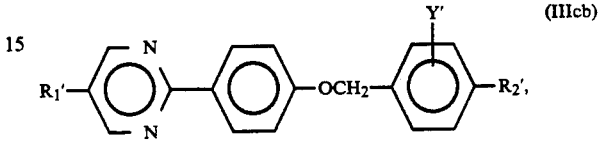 (IIIcb)

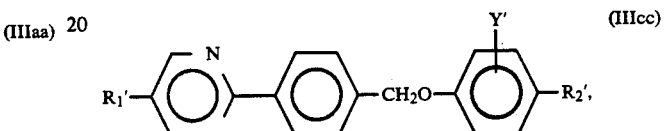 (IIIcc)

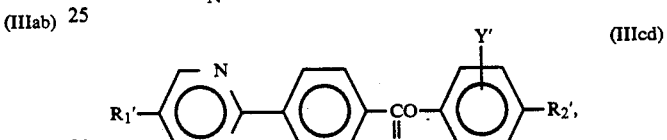 (IIIcd)

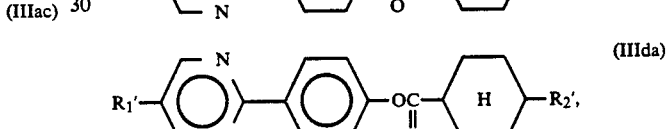 (IIIda)

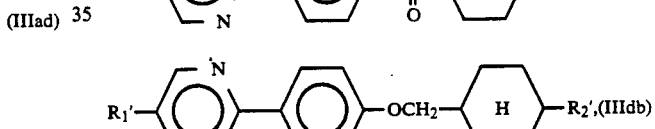 (IIIdb)

and

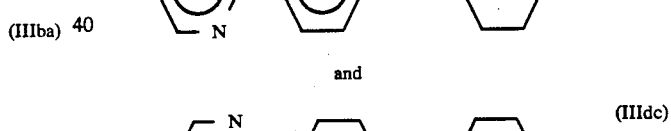 (IIIdc)

In the above-mentioned formula (IV), more preferred compounds thereof may include those represented by the formulas (IVaa) to (IVcd):

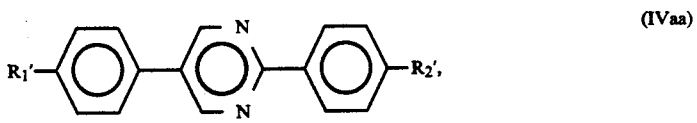 (IVaa)

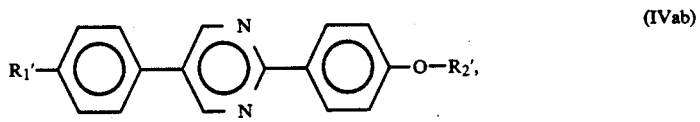 (IVab)

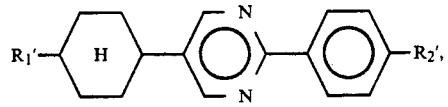
(IVba)
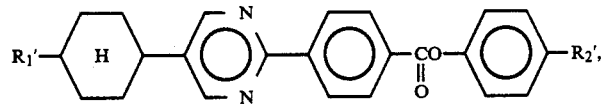
(IVca)
and
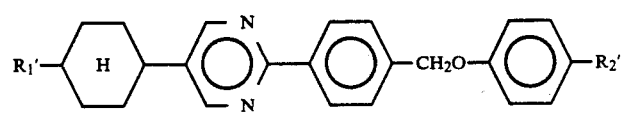
(IVcb)
In the above-mentioned formula (V), more preferred compounds thereof may include those represented by the formulas (Vaa) to (Vbf):
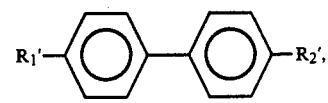
(Vaa)
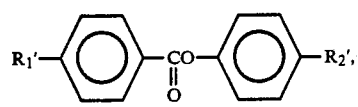
(Vab)
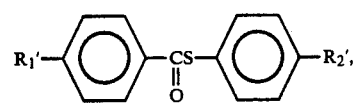
(Vac)
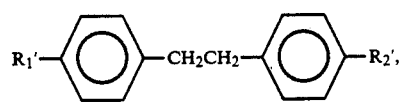
(Vad)
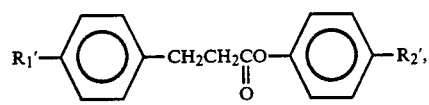
(Vae)
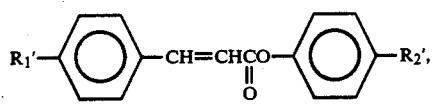
(Vaf)
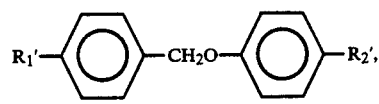
(Vag)
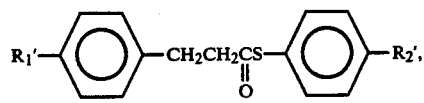
(Vah)
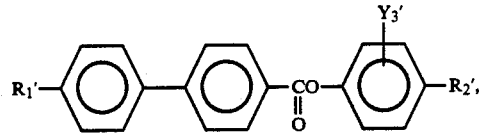
(Vba)
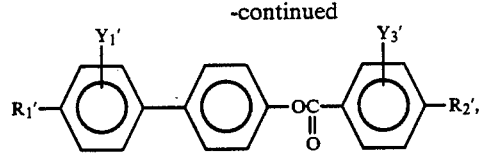
(Vbb)
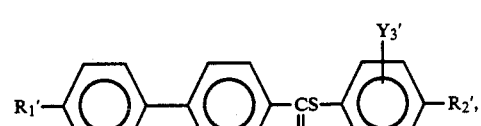
(Vbc)
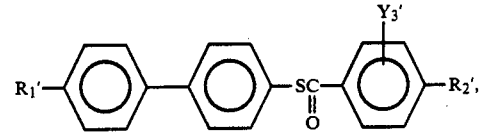
(Vbd)
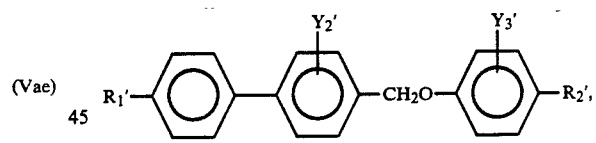
(Vbe)
and
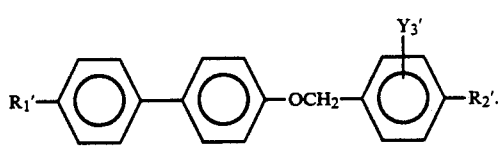
(Vbf)
In the above-mentioned formula (VI), more preferred compounds thereof may include those represented by the formulas (VIaa) to (VIfa):
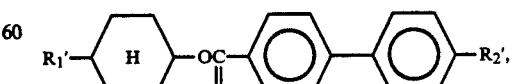
(VIaa)
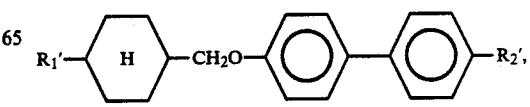
(VIab)

-continued (VIba)

R₁'—[H]—[H]—OC(=O)—⌬—R₂', (VIbb)

R₁'—[H]—[H]—OCH₂—⌬—R₂', (VIda)

R₁'—[H]—⌬—CO(=O)—⌬—R₂', (VIea)

R₁'—⌬—[H]—CO(=O)—⌬—R₂', and (VIfa)

R₁'—[H]—CO(=O)—⌬—R₂'.

(VII)

R₃'—X₁'—[naphthyl]—(X₃'—⌬—)_E X₂'—R₄' wherein E denotes 0 or 1; and $X_1'$ and $X_2'$ respectively denote a single bond, —CO—, —OC—, —O— or —OCO—;
   ‖         ‖              ‖
   O         O              O and $X_3'$ denotes a single bond, —CO—, —OC—, —CH₂O— or —OCH₂—.
   ‖         ‖
   O         O In the above formula (VII), preferred compounds thereof may include those represented by the following formulas (VIIa) and (VIIb):

(VIIa)

R₃'—[naphthyl]—CO(=O)—⌬—R₄', and (VIIb)

R₃'—[naphthyl]—OC(=O)—⌬—R₄'.

In the above formula (VIII), preferred compounds thereof may include those represented by the following formulas (VIIIa) and (VIIIb).

(VIIIa)

R₃'—⌬—[pyrazine]—R₄', and (VIIIb)

R₃'—⌬—[pyrazine]—X₁'—⌬—R₄'.

More preferred compounds of the formula (VIII) may include those represented by the formulas (VIIIaa) to (VIIIbb):

(VIIIaa)

R₃'—⌬—[pyrazine]—R₄', (VIII)

R₃'—X₁'—(⌬—)_F X₃'—[pyrazine]—X₄'—(⌬—)_G X₂'—R₄' wherein F and G respectively denote 0 or 1; $X_1'$ and $X_2'$ respectively denote a single bond, —CO—, —OC— or —O—;
   ‖         ‖
   O         O and $X_3'$ and $X_4'$ respectively denote a single bond, —CO—, —OC—, —CH₂O— or —OCH₂—.
   ‖         ‖
   O         O (VIIIba)

R₃'—⌬—[pyrazine]—CO(=O)—⌬—R₄', and (VIIIbb)

R₃'—⌬—[pyrazine]—OC(=O)—⌬—R₄'.

Herein, $R_3'$ and $R_4'$ respectively denote a linear or branched alkyl group having 1–18 carbon atoms capable of including one or two or more non-neighboring methylene groups which can be replaced with -CH halogen- and capable of further including one or two or more non-neighboring methylene groups other than those directly connected to $X_1'$ or $X_2'$ which can be replaced with at least one species of $$-O-, -\underset{\underset{O}{\|}}{C}-, -O\underset{\underset{O}{\|}}{C}-, -\underset{\underset{O}{\|}}{C}O-, -\underset{\underset{CN}{|}}{C}H- \text{ and } -\underset{\underset{CH_3}{|}}{\overset{CN}{C}}-,$$

with proviso that $R_3'$ and $R_4'$ respectively do not connect to a ring structure by a single bond when $R_3'$ and $R_4'$ respectively denote a halogenated alkyl group containing one methylene group replaced with -CH halogen-.

Further, preferred examples of $R_3'$ and $R_4'$ may respectively include those represented by the following groups (i) to (vii):

i) a linear alkyl group having 1-15 carbon atoms;

ii) $+CH_2\!\!\!\rightarrow_p\!CH-C_qH_{2q+1}$ with $CH_3$ branch wherein p denotes an integer of 0-5 and q denotes an integer of 1-11 (optically active or inactive);

iii) $+CH_2\!\!\rightarrow_r\!CH+CH_2\!\!\rightarrow_s\!OC_tH_{2t+1}$ with $CH_3$ branch wherein r denotes an integer of 0-6, s denotes 0 or 1, and t denotes an integer of 1-14 (optically active or inactive);

iv) $+CH_2\!\!\rightarrow_u\!CH-C_vH_{2v+1}$ with F branch wherein u denotes an integer of 0 or 1 and v denotes an integer of 1-16;

v) $-\underset{\underset{O}{\|}}{C}HCOC_wH_{2w+1}$ with $CH_3$ branch wherein w denotes an integer of 1-15 (optically active or inactive);

vi) $+CH_2\!\!\rightarrow_A\!CH-C_BH_{2B+1}$ with CN branch wherein A denotes an integer of 0-2 and B denotes an integer of 1-15 (optically active or inactive); and vii) $+CH_2\!\!\rightarrow_C\!C-C_DH_{2D+1}$ with CN and $CH_3$ branches wherein C denotes an integer of 0-2 and D denotes an integer of 1-15 (optically active or inactive).

$$R_5'-X_1'+\!\!\bigcirc\!\!-X_3'\!\!\rightarrow_H\!A_1'-X_4'-\!\!\bigcirc\!\!-X_5'-\!\!\bigcirc\!\!\rightarrow_J X_2'-R_6' \quad (IX)$$

wherein H and J respectively denote 0 or 1 with proviso that H+J=0 or 1; $X_1'$ and $X_2'$ respectively denote a single bond, $$-\underset{\underset{O}{\|}}{C}O-, -O\underset{\underset{O}{\|}}{C}- \text{ or } -O-;$$

$A_1'$ denotes a pyridazine ring, pyridine ring, or pyridine ring (isomer);

and $X_3'$ and $X_4'$ respectively denote a single bond, $$-\underset{\underset{O}{\|}}{C}O-, -O\underset{\underset{O}{\|}}{C}-, -CH_2O- \text{ or } -OCH_2-.$$

$$R_5'-X_1'-A_2'-X_3'-\!\!\bigcirc\!\!-X_4'-\!\!\bigcirc\!\!H\!\!-X_2'-R_6' \quad (X)$$

wherein $X_1'$ and $X_2'$ respectively denote a single bond, $$-\underset{\underset{O}{\|}}{C}O-, -O\underset{\underset{O}{\|}}{C}- \text{ or } -O-;$$

$A_2'$ denotes a pyridine ring or pyridine ring (isomer);

and $X_3'$ and $X_4'$ respectively denote a single bond, $$-\underset{\underset{O}{\|}}{C}O-, -O\underset{\underset{O}{\|}}{C}-, -CH_2O- \text{ or } -OCH_2-.$$

$$R_5'-X_1'-A_3'-X_3'-\!\!\bigcirc\!\!-\!\!\bigcirc_{N}^{N}\!\!-X_2'-R_6' \quad (XI)$$

wherein $X_1'$ and $X_2'$ respectively denote a single bond, $$-\underset{\underset{O}{\|}}{C}O-, -O\underset{\underset{O}{\|}}{C} \text{ or } -O-;$$

$A_3'$ denotes

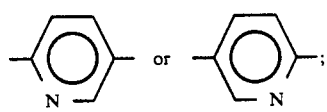

and $X_3'$ respectively denotes a single bond,

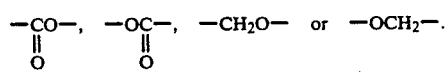

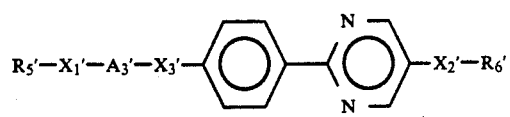

In the above formula (IX), preferred compounds thereof may include those represented by the following formulas (IXa) to (IXc):

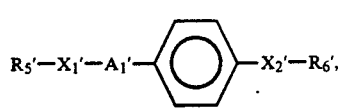

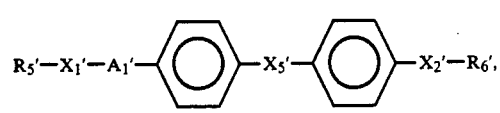

and

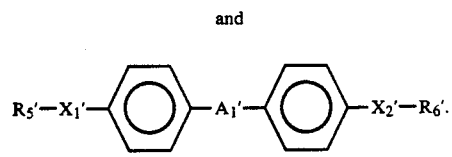

In the above formula (X), preferred compounds thereof may include those represented by the following formulas (Xa) and (Xb):

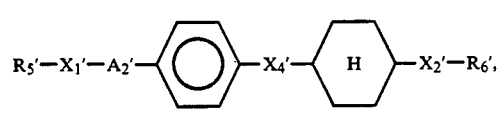

and

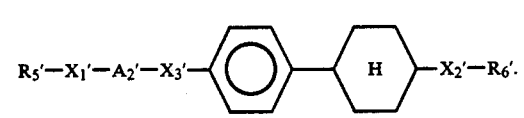

In the above-mentioned formula (IX), more preferred compounds thereof may include those represented by the formulas (IXaa) to (IXcc):

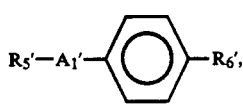

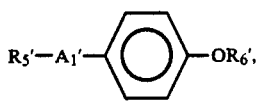

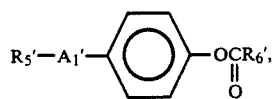

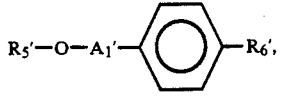

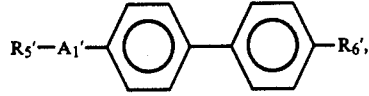

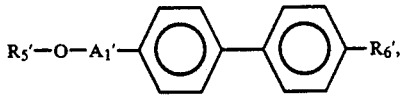

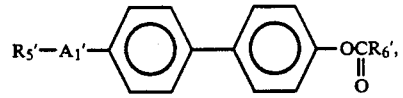

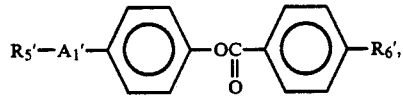

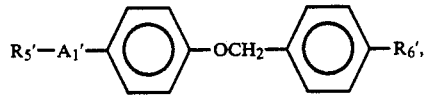

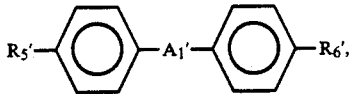

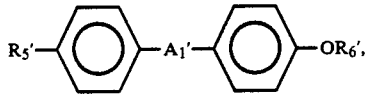

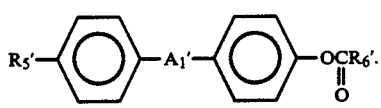

and

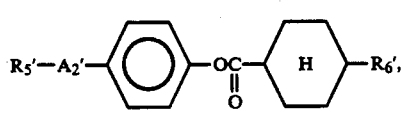

In the above-mentioned formula (X), more preferred compounds thereof may include those represented by the formulas (Xaa) to (Xbb):

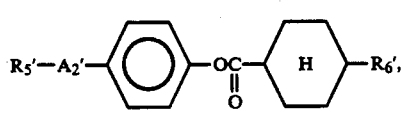

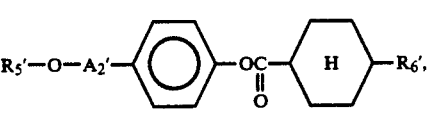

-continued

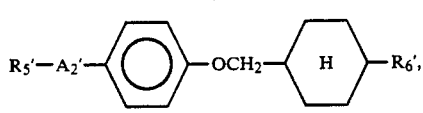

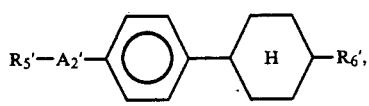

and

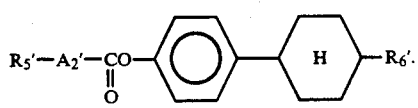

In the above formula (XI), preferred compounds thereof may include those represented by the following formulas (XIa) to (XIg):

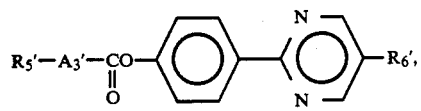 (XIa)

(XIb)

(XIc)

(XId)

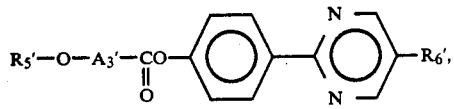 (XIe)

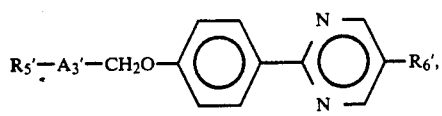 (XIf)

and

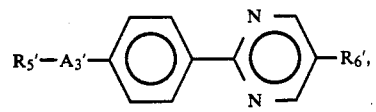 (XIg)

Herein, $R_5'$ and $R_6'$ respectively denote a linear or branched alkyl group having 1-18 carbon atoms capable of including one or two or more non-neighboring methylene groups other than those directly connected to $X_1'$ or $X_2'$ which can be replaced with at least one species of

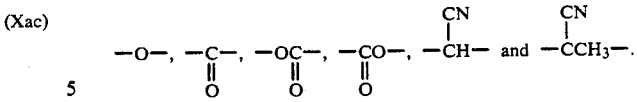 (Xac)

Further, preferred examples of $R_5'$ and $R_6'$ may respectively include those represented by the following groups (i) to (vi):

i) a linear alkyl group having 1-15 carbon atoms;

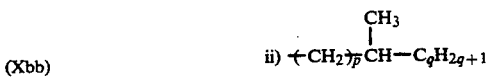

wherein p denotes an integer of 0-5 and q denotes an integer of 1-11 (optically active or inactive);

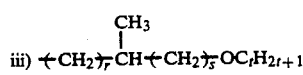

wherein r denotes an integer of 0-6, s denotes 0 or 1, and t denotes an integer of 1-14 (optically active or inactive);

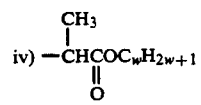

wherein w denotes an integer of 1-15 (optically active or inactive);

wherein A denotes an integer of 0-2 and B denotes an integer of 1-15 (optically active or inactive); and

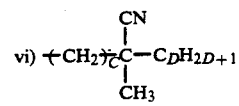

wherein C denotes an integer of 0-2 and D denotes an integer of 1-15 (optically active or inactive).

In formulating the liquid crystal composition according to the present invention, the liquid crystal composition may desirably contain 1-80 wt. %, preferably 1-60 wt. %, more preferably 1-40 wt. % of a mesomorphic compound represented by the formula (I).

Further, when two or more species of the compounds represented by the formula (I) are used, the liquid crystal composition may desirably contain 1-80 wt. %, preferably 1-60 wt. %, more preferably 1-40 wt. %, of the two or more species of the compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å-1 micron, preferably 30-3000 Å, further preferably 50-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
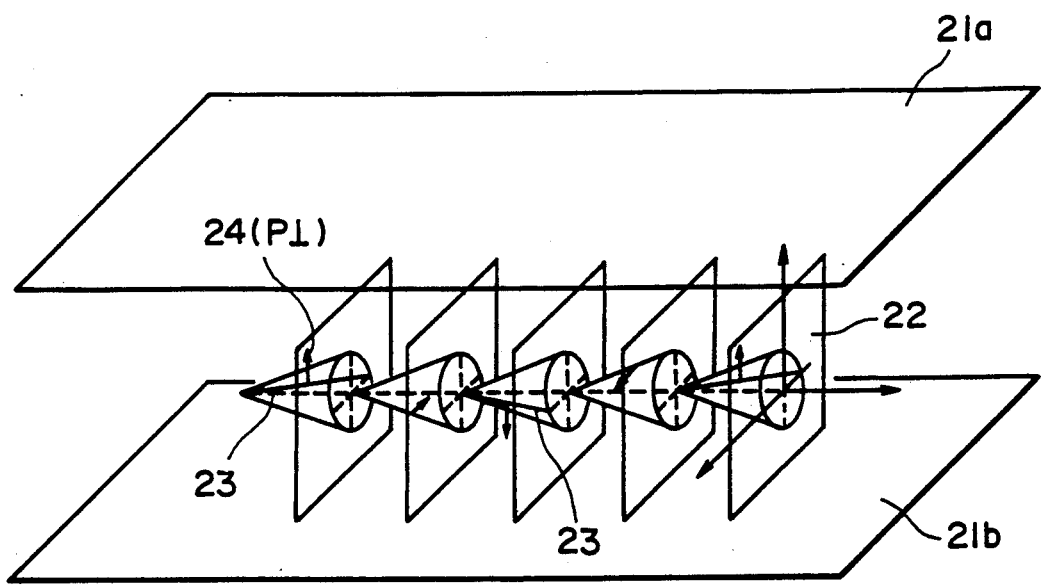
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P_\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
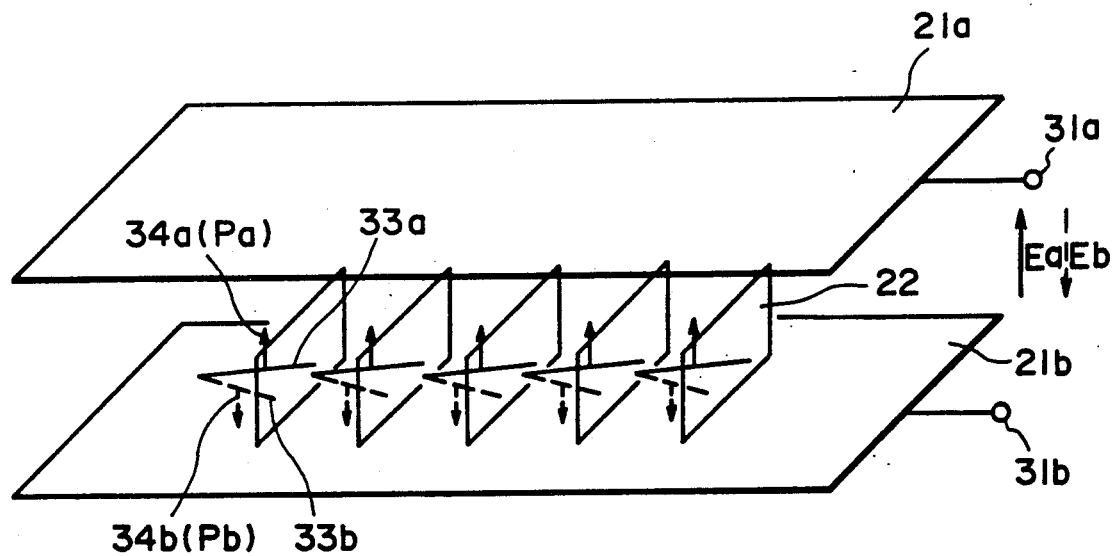

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
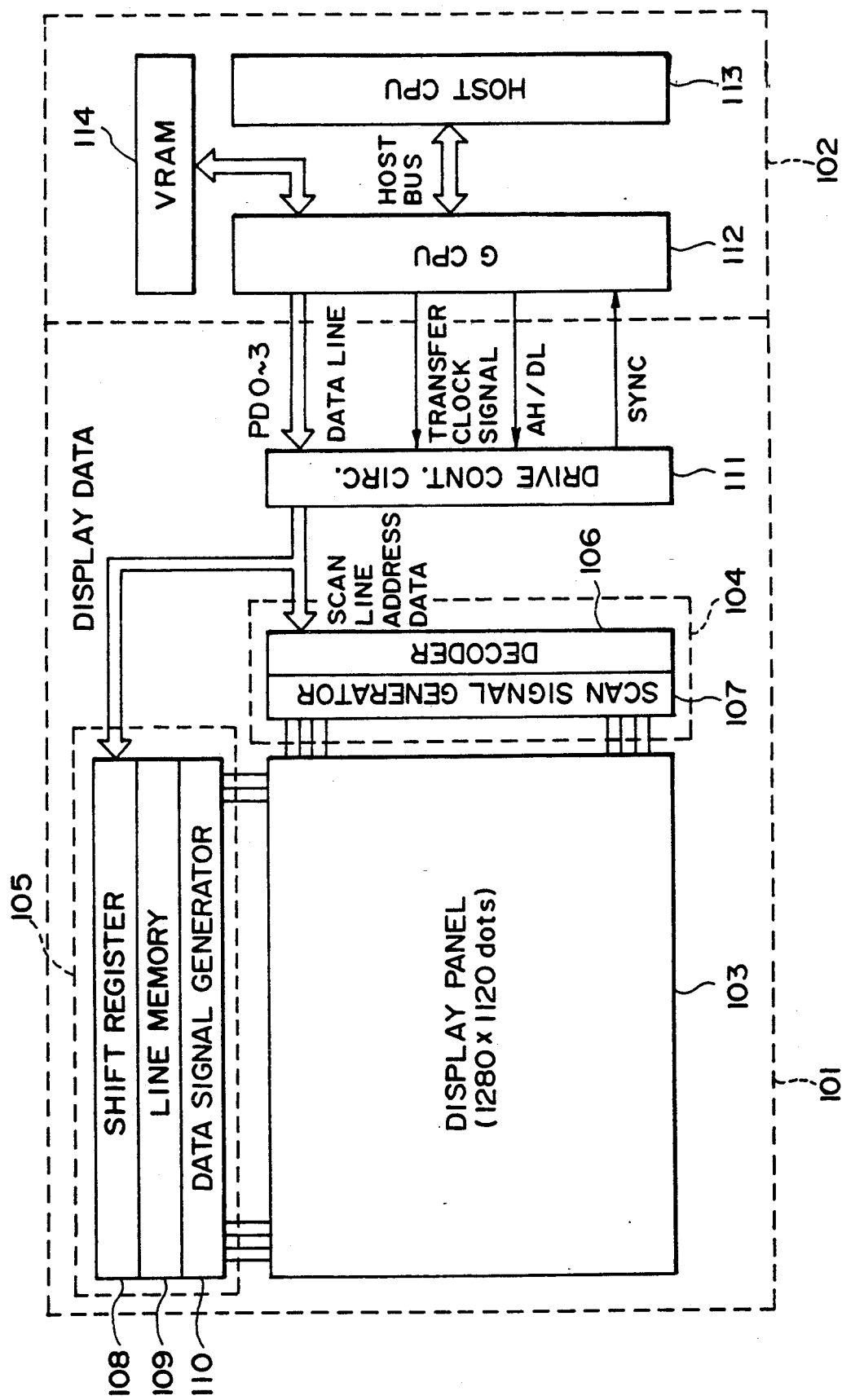
FIG. 4 is a block diagram showing a display apparatus comprising a liquid crystal device utilizing ferroelectricity of a liquid crystal composition and a graphic controller.
Figure 5:
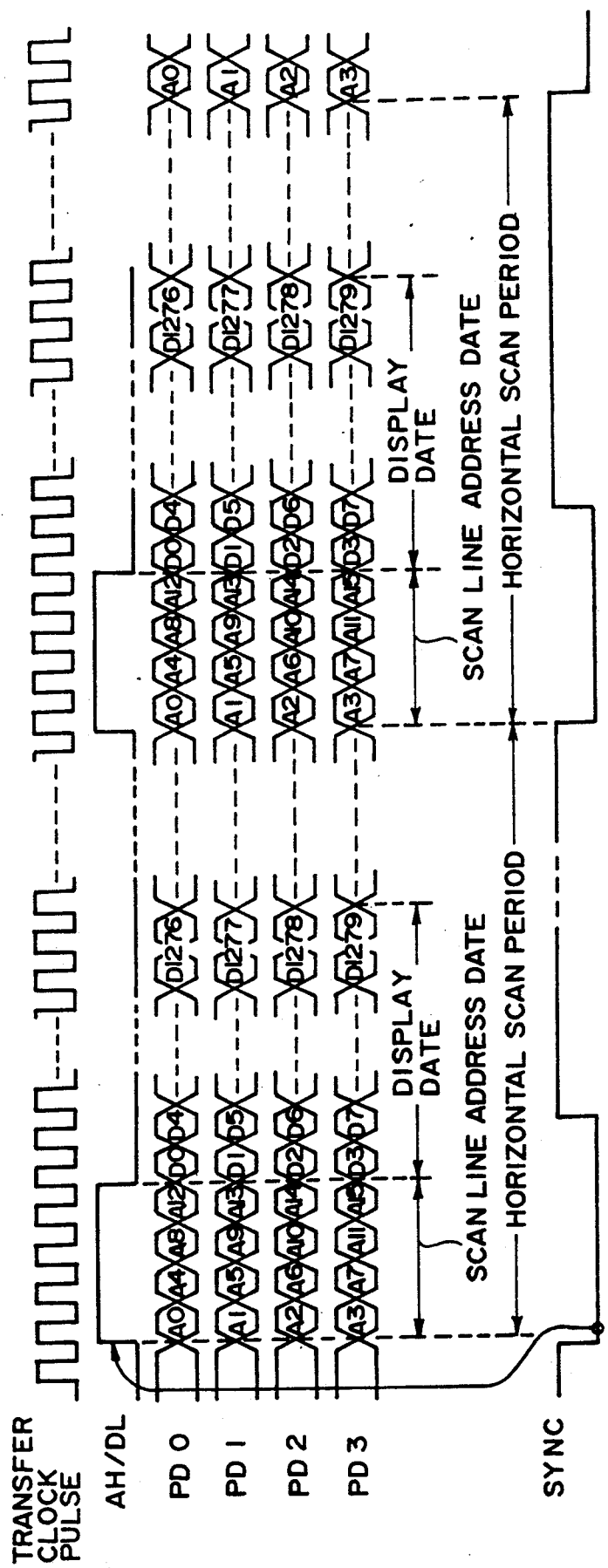
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

6-decyloxy-2-naphthoic acid 3-(butyldimethylsilyl)propyl (Example Compound No. I-5) was synthesized through the following reaction scheme.

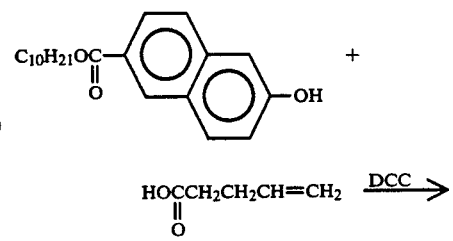

1.0 g (3.0 mM) of 6-decyloxy-2-naphthoic acid, 0.52 g (3.0 mM) of butyldimethyl-3-hydroxypropylsilane and 20 ml of dichloromethane were mixed at room temperature. To the mixture, 0.58 g (2.8 mM) of N,N'-dicyclohexylcarbodiimide (DCC) and 0.05 g of 4-pyrrolidonepyridine were added under stirring, followed by stirring for 20 hours at room temperature. The resultant dicyclohexylurea was recovered by filtration, followed by washing with dichloromethane to be added to the filtrate. The resultant dichloromethane solution was condensed under reduced pressure, followed by purification by silica gel column chromatography (eluent: toluene/hexane=5/1) to obtain 0.98 g of 6-decyloxy-2-naphthoic acid 3-(butyldimethylsilyl)propyl (Yield: 72.3%).

Phase transition temperature (°C.)

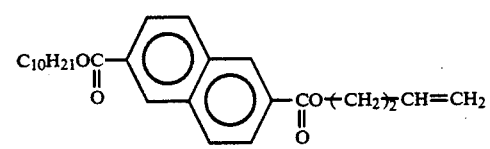

Cryst.: crystal,
SmA: smectic A phase, and
Iso.: isotropic phase.

EXAMPLE 2

5-(butyldimethylsilyl)butanoic acid 2-(6-decyloxycarbonyl)naphthyl (Example Compound No. I-4) was synthesized through the following reaction steps i) and ii).

i)

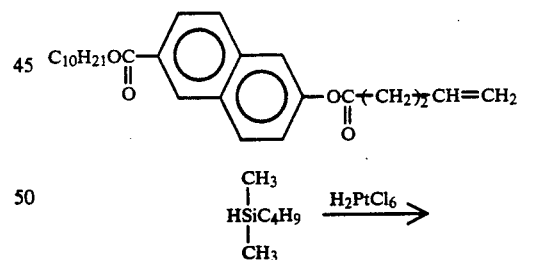

ii)

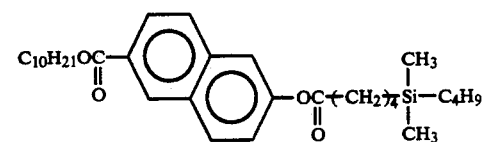

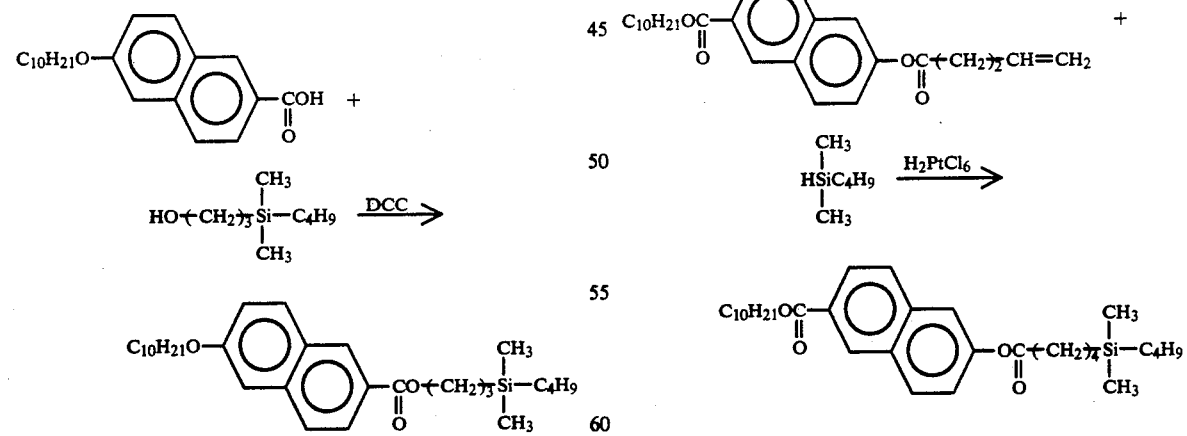

Step i) Production of 4-pentenic acid 2-(6-decyloxycarbonyl)naphthyl 5 ml of dichloromethane was added to 0.30 g (3.05 mM) of 4-pentenic acid, followed by addition of 1.0 g (3.05 mM) of 6-hydroxy-2-naphthoic acid decyl and 1 ml of tetrahydrofuran to provide a solution. To the solution, 0.63 g (3.05 mM) of N,N'-dicyclohexylcarbodiimide, 0.05 g or 4-pyrrolidinopyridine and 5 ml of dichloromethane were added, followed by stirring for 20 hours at room temperature. The resultant dicyclohexylurea was recovered by filtration, followed by washing with dichloromethane to be added to the filtrate. The resultant dichloromethane solution was condensed under reduced pressure, followed by purification by silica gel column chromatography (eluent: toluene) to obtain 1.13 g of 4-pentenic acid 2-(6-decyloxycarbonyl)naphthyl (Yield: 90.4%). Step ii) Production of 5-(butyldimethylsilyl)butanic acid 2-(6-decyloxycarbonyl)naphthyl 2 ml of toluene was added to 1.13 g (2.76 mM) of 4-pentenic acid 2-(6-decyloxycarbonyl)naphthyl, followed by stirring at room temperature. To the mixture, an appropriate amount chloroplatinic acid, ten drops of isopropyl alcohol and 0.35 g (3.03 mM) of butyldimethylsilane were successively added and heated to 80° C., followed by stirring for 5 hours. After the reaction, the reaction mixture was poured into 50 ml of water, followed by extraction with ethyl acetate. The organic layer was washed with water and dried with anhydrous magnesium sulfate. The magnesium sulfate in the resultant organic layer was filtered off, followed by distilling-off of the solvent and purification by silica gel column chromatography (eluent: toluene/hexane=10/2) to obtain 0.21 g of 5-(butyldimethylsilyl)butanic acid 2-(6-decyloxycarbonyl)naphthyl (Yield: 14.5%).

Phase transition temperature (°C.)

Cryst. $\underset{-38}{\overset{5}{\rightleftarrows}}$ Iso.

EXAMPLE 3

Trans-4-pentylcyclohexanecarbonic acid 6-[3-(trimethylsilyl)propoxy]-2-naphthyl (Example Compound No. I-21) was synthesized through the following reaction steps i) to iii).

i)
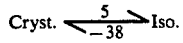

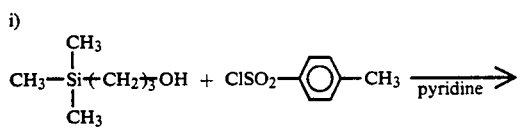

ii)
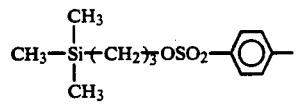

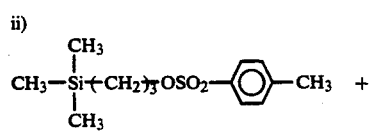

iii)
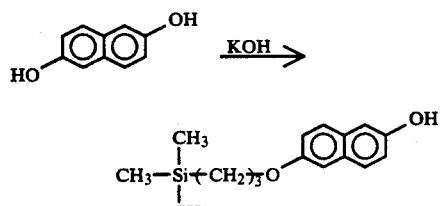

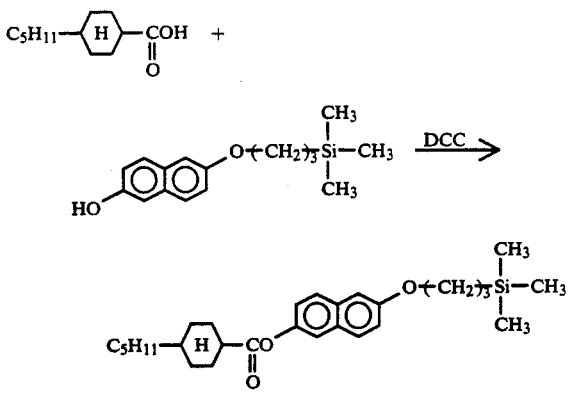

Step i) Production of p-toluenesulfonic acid 3-(trimethylsilyl)propyl 50 ml of pyridine was added to 5.0 g (37.8 mM) of 3-(trimethylsilyl)propanol, followed by stirring. Under cooling on an ice bath, 7.2 g (37.8 mM) of p-toluenesulfonyl chloride was added to the mixture, followed by stirring for 1 hour and then stirring for 5 hours at room temperature. After the reaction, the reaction mixture was poured into cold water and acidified (pH=1) with hydrochloric acid, followed by extraction with ethyl acetate. The organic layer was washed with water and dried with anhydrous magnesium sulfate. The magnesium sulfate in the resultant organic layer was filtered off and the filtrate was condensed into an objective 8.5 g of p-toluenesulfonic acid 3-(trimethylsilyl)propyl (Yield: 78.6%). Step ii) Production of 6-[3-(trimethylsilyl)propyl]-2-hydroxynaphthalene 2.4 g (14.54 mM) of 2,6-dihydroxynaphthalene, 0.76 g (11.49 mM) of 85%-potassium hydroxide aqueous solution, 4 ml of methanol and 20 ml of ethanol were mixed. To the mixture, 3.0 g (10.47 mM) of p-toluenesulfonic acid 3-(trimethylsilyl)propyl were added dropwise in 35 minutes at 65° C. under stirring, followed by stirring for 30 minutes at 65° C. and stirring for 5.5 hours at 80° C. After the reaction, the reaction mixture was poured into cold water and acidified (ph=1) with hydrochloric acid, followed by extraction with ethyl acetate. The organic layer was washed with water and dried with anhydrous magnesium sulfate. The magnesium sulfate in the resultant organic layer was filtered off and the filtrate was condensed, followed by purification by silica gel column chromatography (eluent: chloroform) to obtain 1.12 g of 6-[3-(trimethylsilyl)propyl]-2-hydroxynaphthalene (Yield: 39.0%).

Step iii) Production of trans-4-pentylcyclohexanecarbonic and 6-[3-(trimethylsilyl)propyl]-2-naphthyl 10 ml of dichloromethane was added to 0.36 g (1.82 mM) of trans-4-pentylcyclohexanecarbonic acid and 0.50 g (1.82 mM) of 6-[3-(trimethylsilyl)propyl]-2-hydroxynaphthalene. To the mixture, 0.37 g (1.80 mM) of N,N'-dicyclohexylcarbodiimide (DCC) and 0.02 g of 4-pyrrolidinopyridine were added at room temperature under stirring, followed by stirring for 22 hours at room temperature. The resultant dicyclohexylurea was recovered by filtration, followed by washing with dichloromethane to be added to the filtrate. The resultant dichloromethane solution was condensed under reduced pressure, followed by purification by silica gel column chromatography (eluent: toluene/hexane=3/1) and recrystallization from a mixture solvent of toluene and methanol to obtain 0.67 g of trans-4-pentylcyclohexanecarbonic acid 6-[3-(trimethylsilyl)propoxy]-2-naphthyl (Yield: 80.5%).

Phase transition temperature (°C.)

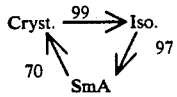

EXAMPLE 4

3-fluoro-4-dodecyloxybenzoic acid 6-[3-(trimethylsilyl)propyl]-2-naphthyl (Example Compound No. I-9) was synthesized through the following reaction scheme.

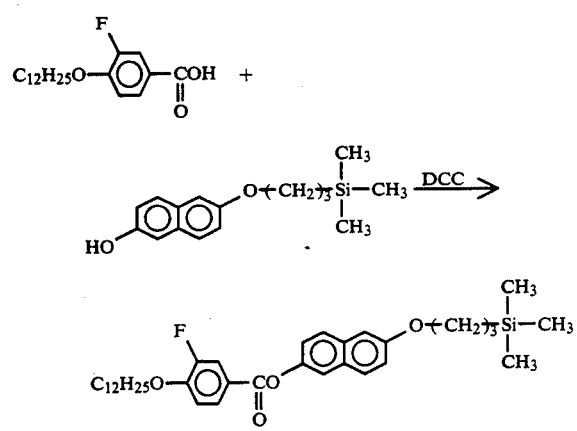

0.59 g (1.82 mM) of 3-fluoro-4-decyloxybenzoic acid, 0.5 g (1.82 mM) of 6-[3-(trimethylsilyl)propyl]-2-hydroxynaphthalene, 10 ml of dichloromethane and 10 ml of tetrahydrofuran were mixed at room temperature. To the mixture, 0.38 g (1.82 mM) of N,N'-dicyclohexylcarbodiimide (DCC) and 0.02 g of 4-pyrrolidonepyridine were added under stirring, followed by stirring for 20 hours at room temperature. The resultant dicyclohexylurea was recovered by filtration, followed by washing with dichloromethane to be added to the filtrate. The resultant dichloromethane solution was condensed under reduced pressure, followed by purification by silica gel column chromatography (eluent: toluene) and recrystallization from a mixture solvent of ethanol and ethyl acetate to obtain 0.86 g of 3-fluoro-4-dodecyloxybenzoic acid 6-[3-(trimethylsilyl)propyl]-2-naphthyl (Yield: 81.1%).

Phase transition temperature (°C.)

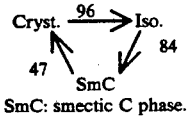

SmC: smectic C phase.

EXAMPLE 5

4-nonyloxybenzoic acid 6-[3-(butyldimethylsilyl)-propyloxycarbonyl]-2-naphthyl (Example Compound No. I-13) was synthesized through the following reaction steps i) and ii).

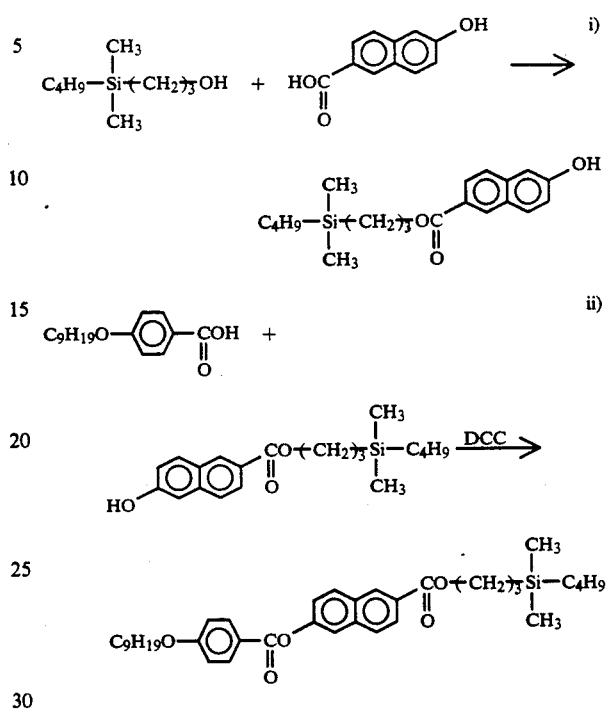

Step i) Production of 6-hydroxy-2-naphthoic acid 3-(butyldimethylsilyl)propyl 2.0 g (10.6 mM) of 6-hydroxy-2-naphthoic acid, 3.71 g (21.3 mM) of butyldimethyl-3-hydroxypropylsilane, 0.25 g (1.31 mM) of p-toluenesulfonic acid and 30 ml of xylene were mixed, followed by refluxing for 6 hours under stirring. After the reaction, the reaction mixture was cooled at room temperature, followed by distilling-off of the solvent under reduced pressure. The residue was washed with hexane and recrystallized from a mixture solvent (isopropyl ether/hexane) to obtain 1.40 g of 6-hydroxy-2-naphthoic acid 3-(butyldimethylsilyl)propyl (Yield: 38.2%). Step ii) Production of 4-nonyloxybenzoic acid 6-[3-(butyldimethylsilyl)propyloxycarbonyl]-2-naphthyl 0.50 g (1.45 mM) of 6-hydroxy-2-naphthoic acid 3-(butyldimethylsilyl)propyl and 0.42 g (1.59 mM) of 4-nonyloxybenzoic acid were mixed. To the mixture, 0.30 g (1.45 mM) of N,N'-dicyclohexylcarbodiimide (DCC), 0.30 g of 4-dimethylaminopyridine were added at room temperature under stirring, followed by stirring for 7 hours at room temperature. The resultant dicyclohexylurea was recovered by filtration, followed by washing with dichloromethane to be added to the filtrate. The resultant dichloromethane solution was condensed under reduced pressure, followed by purification by silica gel column chromatography (eluent: toluene) and recrystallization from a mixture solvent (toluene/methanol) to obtain 0.69 g of 4-nonyloxybenzoic acid 6-[3-butyldimethylsilyl)propyloxycarbonyl]-2-naphthyl (Yield: 80.5%).

Phase transition temperature (°C.)

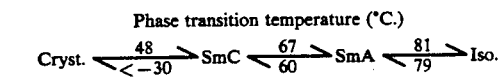

EXAMPLE 6

6-decyloxy-2-naphthoic acid 4-[3-butyldimethyl-silyl)propoxy]phenyl (Example Compound No. I-59) was synthesized through the following reaction steps i) to iii).

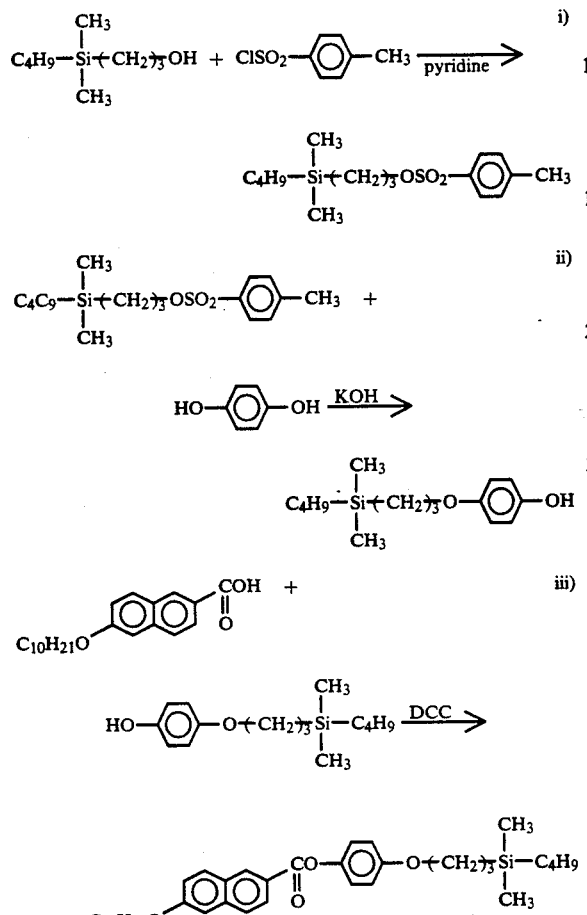

Step i) Production of p-toluenesulfonic acid 3-(butyldimethylsilyl)propyl 50 ml of pyridine was added to 5.0 g (28.68 mM) of butyldimethyl-3-hydroxypropylsilane, followed by stirring. Under cooling on an ice bath, 5.4 g (28.32 mM) of p-toluenesulfonyl chloride was added to the mixture, followed by stirring for 0.5 hour and then stirring for 4 hours at room temperature. After the reaction, the reaction mixture was poured into cold water and acidified (pH=2) with hydrochloric acid, followed by extraction with ethyl acetate. The organic layer was washed with water and dried with anhydrous magnesium sulfate. The magnesium sulfate in the resultant organic layer was filtered off and the filtrate was condensed into an objective 7.6 g of p-toluenesulfonic acid 3-(butyldimethylsilyl)propyl (Yield: 81.7%).

Step ii) Production of 4-[3-(butyldimethylsilyl)-propoxy]phenol 2.32 g (21.1 mM) of hydroquinone, 1.13 g (17.1 mM) of 85%-potassium hydroxide aqueous solution, 6 ml of methanol and 30 ml of ethanol were mixed. To the mixture, 3.0 g (10.47 mM) of p-toluenesulfonic acid 3-(butyldimethylsilyl)propyl were added dropwise in 45 minutes at 65° C. under stirring, followed by stirring for 30 minutes at 65° C. and stirring for 6 hours at 80° C. After the reaction, the reaction mixture was poured into cold water and acidified (ph=2) with hydrochloric acid, followed by extraction with ethyl acetate. The organic layer was washed with water and dried with anhydrous magnesium sulfate. The magnesium sulfate in the resultant organic layer was filtered off and the filtrate was condensed, followed by purification by silica gel column chromatography (eluent: toluene) to obtain 2.05 g of 4-[3-(butyldimethylsilyl)propoxy]-phenol (Yield: 50.6%). Step iii) Production of 6-decyloxy-2-naphthoic acid 4-[3-(butyldimethylsilyl)-propoxy]phenyl 20 ml of dichloromethane was added to 0.62 g (1.89 mM) of 6-decyloxy-2-naphthoic acid and 0.50 g (1.88 mM) of 4-[3-(butyldimethylsilyl)propoxy]phenol. To the mixture, 0.38 g (1.84 mM) of N,N'-dicyclohexylcarbodiimide (DCC) and 0.02 g of 4-pyrrolidinopyridine were added at room temperature under stirring, followed by stirring for 6 hours at room temperature. The resultant dicyclohexylurea was recovered by filtration, followed by washing with dichloromethane to be added to the filtrate. The resultant dichloromethane solution was condensed under reduced pressure, followed by purification by silica gel column chromatography (eluent: toluene) and recrystallization from a mixture solvent (ethanol/ethyl acetate) to obtain 0.83 g of 6-decyloxy-2-naphthoic acid 4-[3-(butyldimethylsilyl)-propoxy]phenyl (Yield: 78.3%).

Phase transition temperature (°C.)

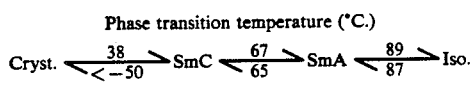

EXAMPLE 7

A liquid crystal composition A was prepared by mixing the following compounds in respectively indicated proportions.

| Structural formula | wt. parts |
|---|---|
| C$_6$H$_{13}$O—⬡—N=⬡=N—C$_8$H$_{17}$ | 46.14 |
| C$_9$H$_{19}$O—⬡—N=⬡=N—C$_8$H$_{17}$ | 23.07 |
| C$_8$H$_{17}$O—⬡—N=⬡=N—C$_{10}$H$_{21}$ | 11.54 |
| C$_3$H$_7$—⟨H⟩—CO—O—⬡—N=⬡=N—C$_{11}$H$_{23}$ | 3.56 |

| Structural formula | wt. parts |
|---|---|
| $C_4H_9$—(H)—CO—O—(benzene)—(pyrimidine N,N)—$C_{11}H_{23}$ | 3.56 |
| $C_5H_{11}$—(H)—CO—O—(benzene)—(pyrimidine N,N)—$C_{11}H_{23}$ | 7.13 |
| $C_{12}H_{25}$—(pyrimidine N,N)—(benzene)—OCH$_2$*CHC$_6$H$_{13}$ (F) | 2.50 |
| $C_{10}H_{21}$—(pyrimidine N,N)—(benzene)—OCH$_2$*CHC$_6$H$_{13}$ (F) | 2.50 |

The liquid crystal composition A was further mixed with the following Example Compound No. I-59 in the proportions indicated below to provide a liquid crystal composition B.

| Ex. Comp. No. | Structural formula | wt. parts |
|---|---|---|
| I-59 | $C_{10}H_{21}O$—(naphthalene)—CO—O—(benzene)—O—(CH$_2$)$_3$—Si(CH$_3$)(CH$_3$)—$C_4H_9$ | 10 |
| | Composition A | 90 |

The liquid crystal composition B showed the following phase transition series.

Phase transition temperature (°C.)

Cryst. $\xrightarrow{8}$ SmC* $\xrightarrow{40}$ SmA $\xrightarrow{67}$ Ch. $\xrightarrow{75}$ Iso.

SmC*: chiral smectic C phase, and
Ch.: cholesteric phase.

EXAMPLE 8

Two 0.7 mm-thick glass plates were provided and respectively coated with an ITO film to form an electrode for voltage application, which was further coated with an insulating layer of vapor-deposited SiO$_2$. On the insulating layer, a 0.2%-solution of silane coupling agent (KBM-602, available from Shinetsu Kagaku K. K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K. K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K. K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 7 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

| | 10° C. | 25° C. |
|---|---|---|
| Response time (μsec) | 538 | 188 |
| Ps (nC/cm2) | 2.8 | 1.7 |

EXAMPLE 9

A liquid crystal composition C was prepared by mixing the following compounds in respectively indicated proportions.

| Structural formula | wt. parts |
|---|---|
| $C_7H_{15}$—(pyrimidine N,N)—(benzene)—OC$_9$H$_{19}$ | 12 |

-continued

| Structural formula | wt. parts |
|---|---|
| C₁₁H₂₃–[pyrimidine]–[phenyl]–OC₆H₁₃ | 10 |
| C₈H₁₇–[pyrimidine]–[phenyl]–O(CH₂)₅*CH(CH₃)CHC₂H₅ | 10 |
| C₁₀H₂₁–[pyrimidine]–[phenyl]–O(CH₂)₄*CH(CH₃)CHOCH₃ | 3 |
| C₈H₁₇–[pyrimidine]–[phenyl]–[phenyl]–OC₆H₁₃ | 8 |
| C₆H₁₃O–[phenyl]–OCO–[naphthyl]–OC₉H₁₉ | 4 |
| C₃H₇–[H]–COO–[phenyl]–[pyrimidine]–C₁₁H₂₃ | 6 |
| C₈H₁₇–[H]–COO–[phenyl]–[pyrimidine]–C₁₁H₂₃ | 2 |
| C₅H₁₁–[H]–COO–[phenyl]–[pyrimidine]–C₁₁H₂₃ | 8 |
| C₁₀H₂₁O–[phenyl]–COO–[phenyl]–OCH₂*CH(CH₃)CH₂C₂H₅ | 15 |
| C₄H₉–[H]–CH₂O–[phenyl]–[pyrimidine]–C₆H₁₃ | 7 |
| C₅H₁₁–[H]–CH₂O–[phenyl]–[pyrimidine]–C₆H₁₃ | 7 |
| C₉H₁₉O–[phenyl]–OCH₂–[phenyl]–[phenyl]–C₇H₁₅ | 4 |
| C₆H₁₃*CH(CH₃)O–[phenyl]–COO–[phenyl]–[phenyl]–OC*CH(CH₃)OC₄H₉ (with C=O) | 2 |

| Structural formula | wt. parts |
|---|---|
| 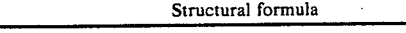 | 2 |

The liquid crystal composition C was further mixed with the following Example Compounds in the proportions indicated below to provide a liquid crystal composition D.

| Ex. Comp. No. | Structural Formula | wt. parts |
|---|---|---|
| I-1 | $C_4H_9O$—◯◯—O—$(CH_2)_3$—Si(CH$_3$)(CH$_3$)—$C_2H_5$ | 1 |
| I-3 | $C_8H_{17}O$—◯◯—OC(=O)—$(CH_2)_2$—Si(CH$_3$)(CH$_3$)—$C_6H_{13}$ | 1 |
| I-8 | $C_6H_{13}$—◯—CO(=O)—◯◯—OCH$_2$—Si(CH$_3$)(CH$_3$)—$C_4H_9$ | 3 |
| I-13 | $C_9H_{19}O$—◯—CO(=O)—◯◯—CO(=O)—$(CH_2)_3$—Si(CH$_3$)(CH$_3$)—$C_4H_9$ | 3 |
| | Composition C | 92 |

A ferroelectric liquid crystal device was prepared in the same manner as in Example 8 except that the above liquid crystal composition D was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 546 | 260 | 143 |

Further, when the device was driven, a clear switching action was observed, and good bistability was shown after the termination of the voltage application.

COMPARATIVE EXAMPLE 1

A ferroelectric liquid crystal device was prepared in the same manner as in Example 8 except that the liquid crystal composition C prepared in Example 9 was injected into a cell. The measured values of the response time of the device were as follows.

| | 10° C. | 25° C. | 40° C. |
|---|---|---|---|
| Response time (μsec) | 784 | 373 | 197 |

EXAMPLE 10

A liquid crystal composition E was prepared by mixing the following example compounds in the indicated proportions with the liquid crystal composition C prepared in Example 9.

| Ex. Comp. No. | Structural Formula | wt. parts |
|---|---|---|
| I-4 | $C_{10}H_{21}OC(=O)$–[naphthalene]–$OC(=O)(CH_2)_4Si(CH_3)(CH_3)$–$C_4H_9$ | 2 |
| I-10 | $C_{16}H_{33}O$–[C$_6$H$_3$F]–$C(=O)O$–[naphthalene]–$O(CH_2)_{10}Si(CH_3)(CH_3)$–$C_6H_{13}$ | 4 |
| I-12 | $C_6H_{13}O$–[phenyl]–$C(=O)O$–[naphthalene]–$OC(=O)CH_2Si(CH_3)(CH_3)$–$C_4H_9$ | 4 |
| Composition C | | 90 |

A ferroelectric liquid crystal device was prepared in the same manner as in Example 8 except that the above liquid crystal composition E was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time ($\mu$sec) | 486 | 234 | 131 |

Further, when the device was driven, a clear switching action was observed, and good bistability was shown after the termination of the voltage application.

EXAMPLE 11

A liquid crystal composition F was prepared by mixing the following example compounds in the indicated proportions with the liquid crystal composition C prepared in Example 9.

| Ex. Comp. No. | Structural formula | wt. parts |
|---|---|---|
| I-57 | $C_8H_{17}O$–[naphthalene]–$C(=O)O$–[phenyl]–$O(CH_2)_3Si(CH_3)(CH_3)$–$C_4H_9$ | 2 |
| I-60 | $C_{12}H_{25}O$–[naphthalene]–$C(=O)O$–[phenyl]–$OC(=O)(CH_2)_4Si(CH_3)(CH_3)$–$C_6H_{13}$ | 2 |
| I-64 | $C_4H_9$–$Si(CH_3)(CH_3)CH_2O$–[naphthalene]–$C(=O)O$–[phenyl]–$OC_8H_{17}$ | 2 |
| I-70 | $C_{10}H_{21}O$–[naphthalene]–$C(=O)O$–[phenyl]–[phenyl]–$OC(=O)(CH_2)_8Si(CH_3)(CH_3)$–$C_{12}H_{25}$ | 1 |

| Ex. Comp. No. | Structural formula | wt. parts |
|---|---|---|
| | Composition C | 93 |

A ferroelectric liquid crystal device was prepared in the same manner as in Example 8 except that the above liquid crystal composition F was used, and the device was subjected to measurement of optical response time and observation of switching states. In the device, a monodomain with a good and uniform alignment characteristic was observed. The result of the measurement are shown below.

| | 10° C. | 25° C. | 40° C. |
|---|---|---|---|
| Response time (μsec) | 593 | 288 | 162 |

EXAMPLE 12

A liquid crystal composition G was prepared by mixing the following compounds in respectively indicated proportions.

| Structural formula | wt. parts |
|---|---|
|  | 10 |
|  | 5 |
|  | 7 |
|  | 7 |
|  | 6 |
|  | 5 |
| 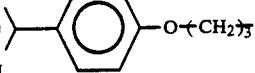 | 5 |
|  | 8 |
|  | 8 |

-continued

| Structural formula | wt. parts |
|---|---|
| C₉H₁₉O—⟨⟩—CO—O—⟨⟩—OC₅H₁₁ | 20 |
| C₈H₁₇—⟨⟩—CO—O—⟨⟩—⟨⟩—OCH₂CHC₂H₅ (CH₃, *) | 5 |
| C₈H₁₇—⟨⟩—O—CO—⟨⟩—⟨⟩—CHOCC₆H₁₃ (CH₃, *, O) | 5 |
| C₆H₁₃—⟨⟩—OCH₂—⟨⟩—⟨⟩—C₇H₁₅ | 6 |
| C₁₂H₂₅—⟨N,N⟩—⟨⟩—OCH₂CHC₆H₁₃ (F, *) | 3 |

The liquid crystal composition G was further mixed with the following Example Compounds in the proportions indicated below to provide a liquid crystal composition H.

A ferroelectric liquid crystal device was prepared in the same manner as in Example 8 except that the above liquid crystal composition H was used, and the device was subjected to measurement of optical response time and observation of switching states. In the device, a monodomain with a good and uniform alignment characteristic was observed. The results of the measurement are shown below.

| Ex. Comp. No. | Structural formula | wt. parts |
|---|---|---|
| I-5 | C₁₀H₂₁O—⟨naphthyl⟩—CO—(CH₂)₃—Si(CH₃)₂—C₄H₉ | 2 |
| I-22 | C₈H₁₇—⟨H⟩—CO—O—⟨naphthyl⟩—CO—(CH₂)₃—Si(CH₃)₂—C₄H₉ | 2 |
| I-31 | C₈H₁₇CO—O—⟨⟩—⟨⟩—CO—O—⟨naphthyl⟩—O—(CH₂)₃—Si(CH₃)₂—CH₃ | 2 |
| I-36 | C₄H₉—Si(CH₃)₂—CH₂O—⟨⟩—⟨⟩—CO—O—⟨naphthyl⟩—OC₁₀H₂₁ | 2 |
| Composition G | | 92 |

|  | 10° C. | 25° C. | 40° C. |
|---|---|---|---|
| Response time (μsec) | 552 | 268 | 139 |

Further, when the device was driven, a clear switching action was observed, and good bistability was shown after the termination of the voltage application.

COMPARATIVE EXAMPLE 2

A ferroelectric liquid crystal device was prepared in the same manner as in Example 8 except that the liquid crystal composition G prepared in Example 12 was injected into a cell. The measured values of the response time of the device were as follows.

| | 10° C. | 25° C. | 40° C. |
|---|---|---|---|
| Response time (μsec) | 653 | 317 | 159 |

EXAMPLE 13

A liquid crystal composition I was prepared by mixing the following example compounds in the indicated proportions with the liquid crystal composition G prepared in Example 12.

| Ex. Comp. No. | Structural formula | wt. parts |
|---|---|---|
| I-20 | [structure] | 3 |
| I-40 | [structure] | 2 |
| I-44 | [structure] | 2 |
| I-46 | [structure] | 2 |
| | Composition G | 91 |

A ferroelectric liquid crystal device was prepared in the same manner as in Example 8 except that the above liquid crystal composition I was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 502 | 246 | 128 |

EXAMPLE 14

A liquid crystal composition M was prepared by mixing the following example compounds in the indicated proportions with the liquid crystal composition G prepared in Example 12.

| Ex. Comp. No. | Structural formula | wt. parts |
|---|---|---|
| I-17 | [structure] | 2 |
| I-28 | [structure] | 1 |

-continued

| Ex. Comp. No. | Structural formula | wt. parts |
|---|---|---|
| I-34 | $C_4H_9OC_2H_4O$—⟨Ph⟩—⟨Ph⟩—COO—⟨Ph⟩—⟨Naph⟩—O$(CH_2)_3$Si$(CH_3)_2$—$C_4H_9$ | 1 |
| I-80 | $C_2H_5Si(CH_3)_2CH_2O$—⟨Naph⟩—COO—⟨Ph⟩—⟨H⟩—$C_8H_{17}$ | 2 |
| Composition G | | 94 |

A ferroelectric liquid crystal device was prepared in the same manner as in Example 8 except that the above liquid crystal composition J was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 594 | 271 | 146 |

EXAMPLE 15

A liquid crystal composition K was prepared by mixing the following compounds in respectively indicated proportions.

| Structural formula | wt. parts |
|---|---|
| $C_9H_{19}$—⟨pyrazine⟩—⟨Ph⟩—$OC_9H_{19}$ | 6 |
| $C_{10}H_{21}$—⟨pyrimidine⟩—⟨Ph⟩—$OC_8H_{17}$ | 6 |
| $C_8H_{17}$—⟨pyridine⟩—⟨Ph⟩—O$(CH_2)_3$*CHC$_2$H$_5$(CH$_3$) | 7 |
| $C_{11}H_{23}O$—⟨pyrimidine⟩—⟨Ph⟩—O$(CH_2)_2$*CHC$_2$H$_5$(CH$_3$) | 14 |
| $C_{10}H_{21}$—⟨pyridine⟩—⟨Ph⟩—$C_6H_{13}$ | 8 |
| $C_6H_{13}$—⟨pyrimidine⟩—⟨Ph⟩—⟨Ph⟩—$C_4H_9$ | 4 |
| $C_8H_{17}$—⟨Ph⟩—⟨pyridine⟩—⟨Ph⟩—$OC_5H_{11}$ | 2 |

-continued

| Structural formula | wt. parts |
|---|---|
| C₃H₇—[H]—CO—O—⟨⟩—⟨N═╲N⟩—C₁₂H₂₅ | 10 |
| C₅H₁₁—[H]—CO—O—⟨⟩—⟨N═╲N⟩—C₁₂H₂₅ | 5 |
| C₁₀H₂₁O—⟨⟩—CS(O)—⟨⟩—OC₈H₁₇ | 10 |
| C₆H₁₃—⟨⟩—CO—O—⟨⟩—⟨⟩—OCH₂CH(CH₃)C₂H₅ | 7 |
| C₃H₇—[H]—CH₂O—⟨⟩—⟨N═╲N⟩—C₈H₁₇ | 7 |
| C₁₀H₂₁—⟨⟩—⟨⟩—OCH₂—⟨⟩—C₇H₁₅ | 5 |
| C₁₂H₂₅—⟨N═╲N⟩—⟨⟩—OCH₂CHFC₅H₁₁* | 2 |
| C₅H₁₁—[H]—CO—O—⟨⟩—OCH₂CHFC₆H₁₃* | 2 |
| C₁₂H₂₅O—⟨⟩—⟨N═╲N⟩—CO—O—(CH₂)₃CH(CH₃)C₂H₅* | 2 |
| C₁₂H₂₅O—⟨⟩—⟨N═╲N⟩—O—(CH₂)₃CH(CH₃)OC₃H₇ | 3 |

The liquid crystal composition K was further mixed with the following Example Compounds in the proportions indicated below to provide a liquid crystal composition L.

| Ex. Comp. No. | Structural formula | wt. parts |
|---|---|---|
| I-9 | C₁₂H₂₅O—⟨F⟩—CO—O—⟨⟩⟨⟩—O—(CH₂)₃Si(CH₃)₃ | 2 |

-continued

| Ex. Comp. No. | Structural formula | wt. parts |
| --- | --- | --- |
| I-18 | [C4H9—Si(CH3)2—CH2O—C6H4—CO-O—naphthalene—COC10H21 (C=O)] | 2 |
| I-51 | [C7H15-pyridine-C6H4—CO-O—naphthalene—O-(CH2)3-Si(CH3)2—CH3] | 2 |
| I-63 | [C8H17O—naphthalene—CO-O—C6H4—CO-O—(CH2)3-Si(CH3)2—C4H9] | 2 |
| Composition K | | 92 |

A ferroelectric liquid crystal device was prepared in the same manner as in Example 8 except that the above liquid crystal composition L was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time ($\mu$sec) | 508 | 266 | 155 |

COMPARATIVE EXAMPLE 3

A ferroelectric liquid crystal device was prepared in the same manner as in Example 8 except that the liquid crystal composition K prepared in Example 15 was injected into a cell. The measured values of the response time of the device were as follows.

|  | 10° C. | 25° C. | 40° C. |
| --- | --- | --- | --- |
| Response time ($\mu$sec) | 668 | 340 | 182 |

EXAMPLE 16

A liquid crystal composition M was prepared by mixing the following example compounds in the indicated proportions with the liquid crystal composition K prepared in Example 15.

| Ex. Comp. No. | Structural formula | wt. parts |
| --- | --- | --- |
| I-59 | [C10H21O—naphthalene—CO-O—C6H4—O-(CH2)3-Si(CH3)2—C4H9] | 2 |
| I-82 | [CH3—Si(CH3)2—(CH2)3O—naphthalene—CO-O—cyclohexyl—cyclohexyl—C6H13] | 1 |
| I-83 | [C2H5—Si(CH3)2—CH2O—naphthalene—CO-O—C6H4—pyridine—C6H13] | 2 |

| Ex. Comp. No. | Structural formula | wt. parts |
|---|---|---|
| I-85 | $C_6H_{13}$—Si(CH₃)(CH₃)—(CH₂)₃—O—[naphthyl]—CO—O—[phenyl-F]—[pyrimidyl]—$C_{11}H_{23}$ | 2 |
| | Composition K | 93 |

A ferroelectric liquid crystal device was prepared in the same manner as in Example 8 except that the above liquid crystal composition M was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 497 | 269 | 164 |

EXAMPLE 17

A liquid crystal composition N was prepared by mixing the following example compounds in the indicated proportions with the liquid crystal composition K prepared in Example 15.

monodomain with a good and uniform alignment characteristic was observed. The results of the measurement are shown below.

| | 10° C. | 25° C. | 40° C. |
|---|---|---|---|
| Response time (μsec) | 449 | 237 | 142 |

EXAMPLE 18

A blank cell was prepared in the same manner as in Example 9 by using a 2% aqueous solution of polyvinyl alcohol resin (PVA-117, available from Kuraray K. K.) instead of the 1.5%-solution of polyimide resin precursor in dimethylacetoamide on each electrode plate. A ferroelectric liquid crystal device was prepared by filling the blank cell with the liquid crystal composition C prepared in Example 9. The liquid crystal device was subjected to measurement of optical response time in

| Ex. Comp. No. | Structural formula | wt. parts |
|---|---|---|
| I-14 | $C_8H_{17}O$—[phenyl-CF₃]—CO—O—[naphthyl]—OC(O)—(CH₂)₈—Si(CH₃)(CH₃)—$C_{12}H_{25}$ | 2 |
| I-19 | $C_4H_9$—Si(CH₃)(CH₃)—(CH₂)₃—O—[phenyl]—CO—O—[naphthyl]—OCC₈H₁₇(O) | 3 |
| I-63 | $C_8H_{17}O$—[naphthyl]—CO—O—[phenyl]—CO—O—(CH₂)₃—Si(CH₃)(CH₃)—$C_4H_9$ | 2 |
| I-78 | $C_2H_5$—Si(CH₃)(CH₃)—CH₂O—[naphthyl]—CO—O—[phenyl]—[phenyl]—COC₈H₁₇(O) | 1 |
| | Composition K | 92 |

A ferroelectric liquid crystal device was prepared in the same manner as in Example 8 except that the above liquid crystal composition N was used, and the device was subjected to measurement of optical response time and observation of switching states. In the device, a the same manner as in Example 8. The results are shown below.

| | 10° C. | 25° C. | 40° C. |
|---|---|---|---|
| Response time (μsec) | 538 | 258 | 144 |

EXAMPLE 19

A blank cell was prepared in the same manner as in Example 9 except for omitting the $SiO_2$ layer to form an alignment control layer composed of the polyimide resin layer alone on each electrode plate. A ferroelectric liquid crystal device was prepared by filling the blank cell with the liquid crystal composition C prepared in Example 9. The liquid crystal device was subjected to measurement of optical response time in the same manner as in Example 8. The results are shown below.

| | 10° C. | 25° C. | 40° C. |
|---|---|---|---|
| Response time (μsec) | 547 | 256 | 142 |

As is apparent from the above Examples 18 and 19, also in the cases of different device structures, the devices containing the ferroelectric liquid crystal composition C according to the present invention respectively provided a remarkably improved operation characteristic at a lower temperature and also a decreased temperature-dependence of the response speed similar to those in Example 9.

EXAMPLE 20 trans-4-pentylcyclohexanecarbonic acid 4-[3-(trimethylsilyl)propoxy]phenyl (n=1) and trans-4-pentylcyclohexanecarbonic acid 4'-[3-(trimethyl)propoxy]-4-biphenyl (n=2) were synthesized through the following reaction schemes, respectively.

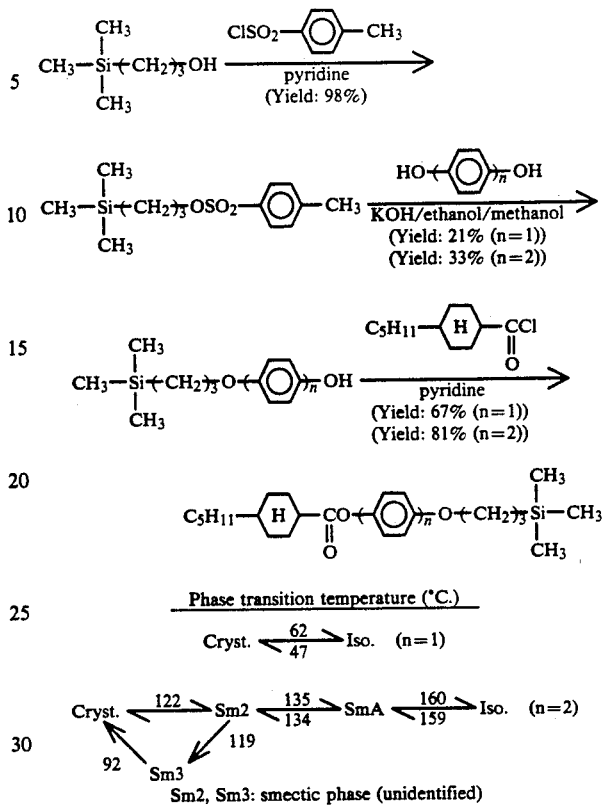

The liquid crystal compositions O, P and Q were prepared by mixing trans-4-pentylcyclohexanecarbonic acid 6-[3-(trimethylsilyl)propoxy]-2-naphthyl (Example Compound No. I-21) prepared in Example 3, the above-prepared trans-4-pentylcyclohexanecarbonic acid 4-[3-(trimethylsilyl)propoxy]phenyl and the above-prepared trans-4-pentylcyclohexanecarbonic acid 4'-[3-(trimethylsilyl)propoxy]-4-biphenyl, respectively, with the liquid crystal composition A prepared in Example 7 in respectively indicated proportions.

| Ex. Comp. No. | Structural Formula | wt. parts |
|---|---|---|
| | [Composition O] | |
| I-21 | $C_5H_{11}$—⟨H⟩—CO—O—⟨naphthyl⟩—O—$(CH_2)_3$—Si$(CH_3)_3$ | 5 |
| | Composition A | 95 |

Phase transition temperature (°C.)

Cryst. ⇌(8/−1) SmC* ⇌(51/51) SmA ⇌(63/63) Ch. ⇌(76/75) Iso.

| | [Composition P] | |
|---|---|---|
| | $C_5H_{11}$—⟨H⟩—CO—O—⟨phenyl⟩—O—$(CH_2)_3$—Si$(CH_3)_3$ | 5 |
| | Composition A | 95 |

| Ex. Comp. No. | Structural Formula | wt. parts |
|---|---|---|

Phase transition temperature (°C.)

Cryst. ⇌(8/−1) SmC* ⇌(48/47) SmA ⇌(62/61) Ch. ⇌(74/74) Iso.

[Composition Q]

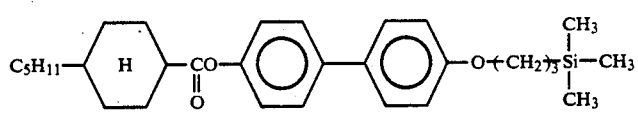

Composition A    95

Phase transition temperature (°C.)

Cryst. ⇌(8/−1) SmC* ⇌(57/56) SmA ⇌(67/67) Ch. ⇌(79/79) Iso.

Ferroelectric liquid crystal devices were prepared in the same manner as in Example 8 except for using the liquid crystal compositions O, P and Q, respectively. The liquid crystal devices were subjected to measurement of optical response time in the same manner as in Example 8. The results are shown below.

| Composition | Response time (μsec) | | |
|---|---|---|---|
| | 10° C. | 30° C. | 40° C. |
| O | 625 | 310 | 217 |
| P | 690 | 332 | 230 |
| Q | 870 | 391 | 271 |

As is apparent from the above results, the composition O containing the mesomorphic compound having a naphthalene skeleton according to the present invention provided improved response speed and a decreased temperature-dependence of response speed compared with the compositions P and Q containing the mesomorphic compounds having a phenyl skeleton and a biphenyl skeleton, respectively.

EXAMPLE 21

4-nonyloxybenzoic acid 5-[6-(butyldimethylsilyl)-propyloxycarbonyl]phenyl was synthesized through the following reaction schemes.

| Composition | Response time (μsec) | |
|---|---|---|
| | 10° C. | 20° C. |
| R | 515 | 217 |
| S | 569 | 230 |

The liquid crystal compositions R and S were prepared by mixing 4-nonyloxybenzoic acid 6-[3-(butyldimethylsilyl)propyloxycarbonyl]-2-naphthyl (Example Compound No. I-13) prepared in Example 5 and 4-nonyloxybenzoic acid 4-[3-(butyldimethylsilyl)-propyloxycarbonyl)phenyl, respectively, with the liquid crystal composition A prepared in Example 7 in respectively indicated proportions.

| Ex. Comp. No. | Structural formula | wt. parts |
|---|---|---|

[Composition R]

I-13

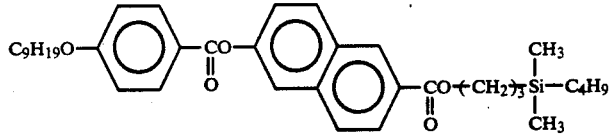

Composition A    95

Phase transition temperature (°C.)

Cryst. ⇌(9/0) SmC* ⇌(45/44) SmA ⇌(68/67) Ch. ⇌(77/76) Iso.

[Composition S]

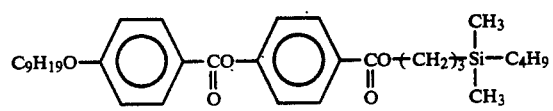

Composition A    95

-continued

| Ex. Comp. No. | Structural formula | wt. parts |
|---|---|---|

Phase transition temperature (°C.)

Cryst. $\underset{0}{\overset{8}{\rightleftarrows}}$ SmC* $\underset{43}{\overset{44}{\rightleftarrows}}$ SmA $\underset{67}{\overset{68}{\rightleftarrows}}$ Ch. $\underset{74}{\overset{75}{\rightleftarrows}}$ Iso.

Ferroelectric liquid crystal devices were prepared in the same manner as in Example 8 except for using the liquid crystal composition R and S, respectively. The liquid crystal devices were subjected to measurement of optical response time in the same manner as in Example 8. The results are shown below.

| Composition | Response time (μsec) | |
|---|---|---|
| | 10° C. | 20° C. |
| R | 515 | 217 |
| S | 569 | 230 |

As is apparent from the above results, the composition R containing the mesomorphic compound having a naphthalene skeleton according to the present invention provided improved response speed and a decreased temperature-dependence of response speed compared with the composition S containing the mesomorphic compound having a phenyl skeleton.

EXAMPLE 22

4-decyloxybenzoic acid 4-[3-(butyldimethylsilyl)-propoxy]phenyl was synthesized through the following reaction scheme.

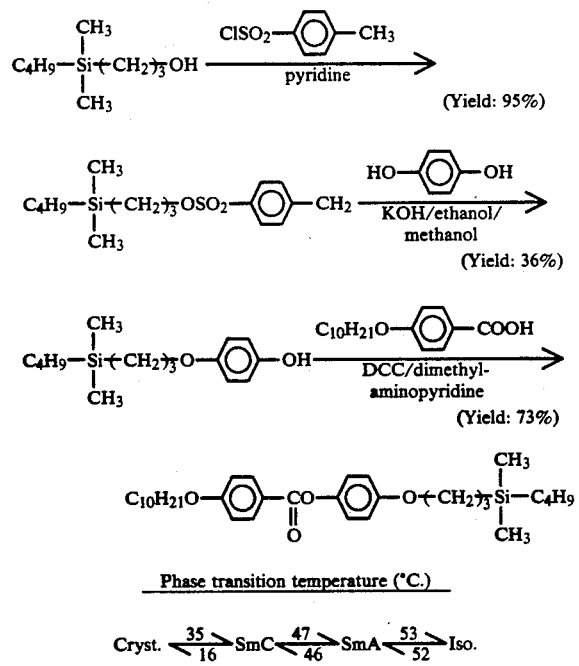

Phase transition temperature (°C.)

Cryst. $\underset{16}{\overset{35}{\rightleftarrows}}$ SmC $\underset{46}{\overset{47}{\rightleftarrows}}$ SmA $\underset{52}{\overset{53}{\rightleftarrows}}$ Iso.

The liquid crystal compositions T was prepared by mixing 4-decyloxybenzoic acid 4-[3-(butyldimethylsilyl)propoxy]phenyl with the liquid crystal composition A prepared in Example 7 in respectively indicated proportions.

| Structural formula | wt. parts |
|---|---|
| [Composition T] C₁₀H₂₁O—⟨⟩—CO—⟨⟩—CO—(CH₂)₃—Si(CH₃)₂—C₄H₉ (with CO as C=O) | 10 |
| Composition A | 90 |

Phase transition temperature (°C.)

Cryst. $\overset{8}{\rightarrow}$ SmC* $\overset{46}{\rightarrow}$ SmA $\overset{66}{\rightarrow}$ Ch. $\overset{72}{\rightarrow}$ Iso.

A ferroelectric liquid crystal device was prepared in the same manner as in Example 8 except for using the liquid crystal composition T. The liquid crystal device was subjected to measurement of optical response time in the same manner as in Example 8. The results are compared with those of the device prepared in Example 8 using the composition B prepared in Example 7 and shown below.

| Composition | Response time (μsec) | |
|---|---|---|
| | 10° C. | 25° C. |
| B | 538 | 188 |
| T | 720 | 245 |

As is apparent from the above results, the composition B containing the mesomorphic compound having a naphthalene skeleton according to the present invention provided improved response speed and a decreased temperature-dependence of response speed compared with the composition T containing the mesomorphic compound having a phenyl skeleton.

As described hereinabove, according to the present invention, there is provided a mesomorphic compound which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic, an improved low-temperature operation characteristic and a decreased temperature-dependence of response speed. The present invention further provides a display apparatus and a display method which employ such a device as a display unit, whereby good display characteristics can be obtained in combination with a light source, a drive circuit, etc.

What is claimed is:

1. A mesomorphic compound represented by the following formula (I):

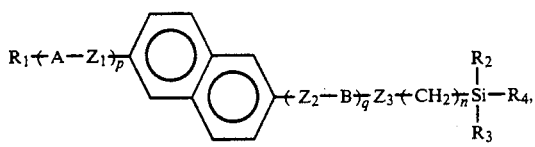
(I)

wherein $R_1$ denotes a linear or branched alkyl group having 2-16 carbon atoms capable of including one or two non-neighboring methylene groups which can be replaced with

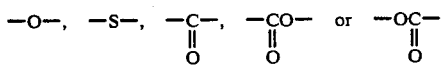

and capable of including fluorine substituted for hydrogen; A denotes $-A_1-$ or $-A_1-A_2-$ and B denotes $-B_1-$ or $-B_1-B_2-$ wherein $A_1$, $A_2$, $B_1$ and $B_2$ respectively denote

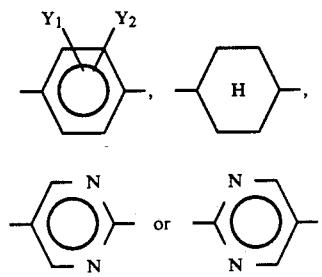

wherein $Y_1$ and $Y_2$ respectively denote H, F, Cl, Br, $-CH_3$, $-CN$ or $-CF_3$; $Z_1$ and $Z_2$ respectively denote

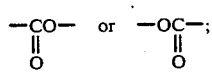

$Z_3$ denotes

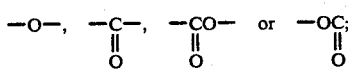

$R_2$, $R_3$ and $R_4$ respectively denote a linear or branched alkyl group having 1-16 carbon atoms including a methylene group which can be replaced with

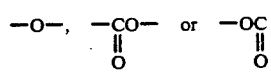

with proviso that it is not adjacent to the silicon atom; p and q are respectively 0 or 1 with proviso that p+q is 0 or 1; and n is an integer of 1-12.

2. A mesomorphic compound according to claim 1, wherein $R_1$ denotes an alkyl group, an alkoxy group, an alkanoyloxy group or an alkoxycarbonyl group.

3. A mesomorphic compound according to claim 1, wherein $A_1$, $A_2$, $B_1$ and $B_2$ respectively denote

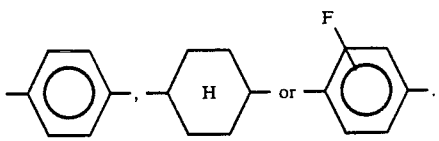

4. A mesomorphic compound according to claim 1, wherein $R_2$, $R_3$ and $R_4$ respectively denote an alkyl group having 1-12 carbon atoms.

5. A liquid crystal composition comprising at least two mesomorphic compounds, at least one of which is a mesomorphic compound of the formula (I) according to claim 1.

6. A liquid crystal composition according to claim 5, which comprises 1-80 wt. % of a mesomorphic compound of the formula (I).

7. A liquid crystal composition according to claim 5, which comprises 1-60 wt. % of a mesomorphic compound of the formula (I).

8. A liquid crystal composition according to claim 5, which comprises 1-40 wt. % of a mesomorphic compound of the formula (I).

9. A liquid crystal composition according to claim 5, which has a chiral smectic phase.

10. A liquid crystal composition according to claim 5, wherein $R_1$ denotes an alkyl group, an alkoxy group, an alkanoyloxy group or an alkoxycarbonyl group.

11. A liquid crystal composition according to claim 5, wherein $A_1$, $A_2$, $B_1$ and $B_2$ respectively denote

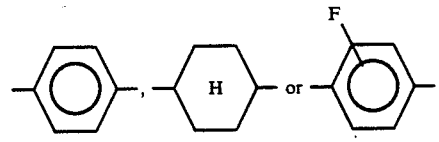

12. A liquid crystal composition according to claim 5, wherein $R_2$, $R_3$ and $R_4$ respectively denote an alkyl group having 1-12 carbon atoms.

13. A liquid crystal device, comprising a pair of electrode plates and a liquid crystal composition according to claim 5 disposed between the electrode plates.

14. A liquid crystal device according to claim 13, wherein $R_1$ denotes an alkyl group, an alkoxy group, an alkanoyl group or an alkylcarbonyl group.

15. A liquid crystal device according to claim 13, wherein $A_1$, $A_2$, $B_1$ and $B_2$ respectively denote

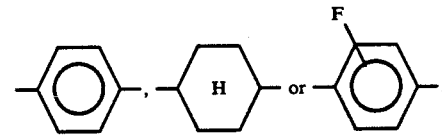

16. A liquid crystal device according to claim 13, wherein $R_2$, $R_3$ and $R_4$ respectively denote an alkyl group having 1-12 carbon atoms.

17. A liquid crystal device according to claim 13, which further comprises an insulating alignment control layer on the electrode plate.

18. A liquid crystal device according to claim 17, wherein the insulating alignment control layer has been subjected to rubbing.

19. A display apparatus comprising a liquid crystal device according to claim 13, and voltage application means for driving the liquid crystal device.

20. A display apparatus according to claim 19, wherein $R_1$ denotes an alkyl group, an alkoxy group, an alkanoyloxy group or an alkoxycarbonyl group.

21. A display apparatus according to claim 19, wherein $A_1$, $A_2$, $B_1$ and $B_2$ respectively denote

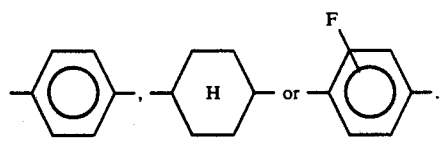

22. A display apparatus according to claim 19, wherein $R_2$, $R_3$ and $R_4$ respectively denote an alkyl group having 1-12 carbon atoms.

23. A display apparatus according to claim 19, which further comprises a drive circuit.

24. A display apparatus according to claim 19, which further comprises a light source.

25. A display method, comprising:
providing a liquid crystal composition comprising at least two mesomorphic compound, at least one of which is a mesomorphic compound of the following formula (I):

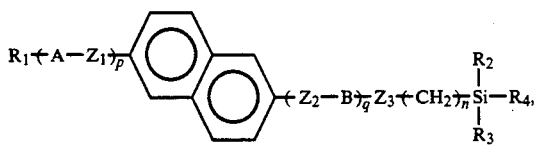

wherein $R_1$ denotes a linear or branched alkyl group having 2-16 carbon atoms capable of including one or two non-neighboring methylene groups which can be replaced with

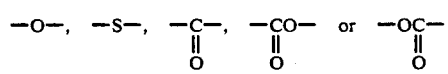

and capable of including fluorine substituted for hydrogen; A denotes —$A_1$— or —$A_1$—$A_2$— and B denotes —$B_1$— or —$B_1$—$B_2$— wherein $A_1$, $A_2$, $B_1$ and $B_2$ respectively denote

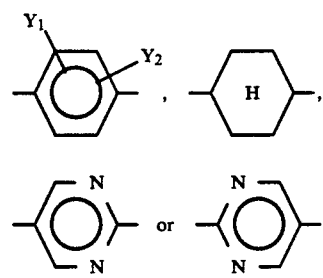

wherein $Y_1$ and $Y_2$ respectively denote H, F, Cl, Br, —$CH_3$, —CN or —$CF_3$; $Z_1$ and $Z_2$ respectively denote

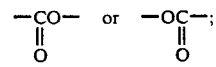

$Z_3$ denotes

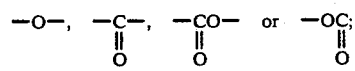

$R_2$, $R_3$ and $R_4$ respectively denote a linear or branched alkyl group having 1-16 carbon atoms including a methylene group which can be replaced with

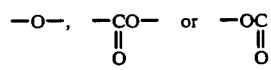

with proviso that it is not adjacent to the silicon atom; p and q are respectively 0 or 1 with proviso that p+q is 0 or 1; and n is an integer of 1-12; and switching the alignment direction of liquid crystal molecules by applying voltages to the liquid crystal composition to effect display.

26. A display method according to claim 25, wherein $R_1$ denotes an alkyl group, an alkoxy group, an alkanoyloxy group or an alkoxycarbonyl group.

27. A display method according to claim 25, wherein $A_1$, $A_2$, $B_1$ and $B_2$ respectively denote

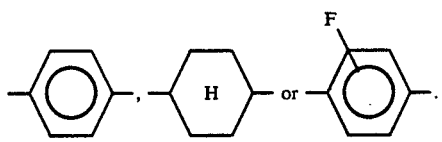

28. A display method according to claim 25, wherein $R_2$, $R_3$ and $R_4$ respectively denote an alkyl group having 1-12 carbon atoms.

29. A display method according to claim 25, wherein the liquid crystal composition comprises 1-80 wt. % of a mesomorphic compound of the formula (I).

30. A display method according to claim 25, wherein the liquid crystal composition comprises 1-60 wt. % of a mesomorphic compound of the formula (I).

31. A display method according to claim 25, wherein the liquid crystal composition comprises 1-40 wt. % of a mesomorphic compound of the formula (I).

32. A display method according to claim 25, wherein the liquid crystal composition assumes a chiral smectic phase.

33. A display method, comprising:
providing a liquid crystal device comprising a pair of electrode plates and a liquid crystal composition disposed therebetween comprising at least two mesomorphic compound, at least one of which is a mesomorphic compound of the following formula (I):

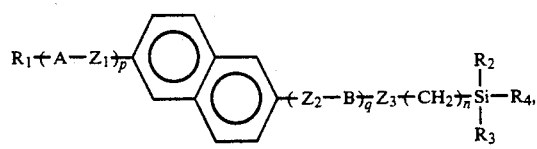 (I)

wherein $R_1$ denotes a linear or branched alkyl group having 2-16 carbon atoms capable of including one or two non-neighboring methylene groups which can be replaced with

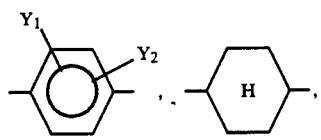

and capable of including fluorine substituted for hydrogen; A denotes —$A_1$— or —$A_1$—$A_2$— and B denotes —$B_1$— or —$B_1$—$B_2$— wherein $A_1$, $A_2$, $B_1$ and $B_2$ respectively denote

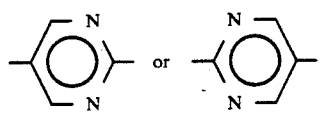

wherein $Y_1$ and $Y_2$ respectively denote H, F, Cl, Br, —$CH_3$, —CN or —$CF_3$; $Z_1$ and $Z_2$ respectively denote

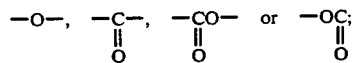

$Z_3$ denotes

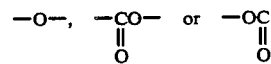

$R_2$, $R_3$ and $R_4$ respectively denote a linear or branched alkyl group having 1-16 carbon atoms including a methylene group which can be replaced with

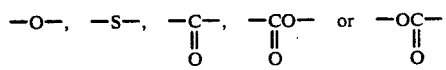

with proviso that it is not adjacent to the silicon atom; p and q are respectively 0 or 1 with proviso that p+q is 0 or 1; and n is an integer of 1-12; and switching the alignment direction of liquid crystal molecules by applying voltages to the liquid crystal composition between the electrode plates to effect display.

34. A display method according to claim 33, wherein $R_1$ denotes an alkyl group, an alkoxy group, an alkanoyloxy group or an alkoxycarbonyl group.

35. A display method according to claim 33, wherein $A_1$, $A_2$, $B_1$ and $B_2$ respectively denote

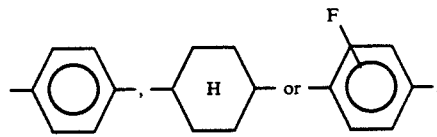

36. A display method according to claim 33, wherein $R_2$, $R_3$ and $R_4$ respectively denote an alkyl group having 1-12 carbon atoms.

* * * * *

UNITED STATES PATENT AND TRADEMARK OFFICE
CERTIFICATE OF CORRECTION

PATENT NO. : 5,188,762
DATED : February 23, 1993
INVENTOR(S) : TAKASHI IWAKI, ET AL.

Page 1 of 3

It is certified that error appears in the above-identified patent and that said Letters Patent is hereby corrected as shown below:

COLUMN 1

Line 31, "on" should read --in--.

COLUMN 38

Line 59, "y" should read --v--.

COLUMN 55

Line 12, "bonyl)naphthyl" should read --bonyl)naphthyl.--.

COLUMN 56

Line 35, "2-hydroxynaphthalene" should read --2-hydroxynaphthalene.--.

COLUMN 58

Line 45, "38.2%). Step ii)" should read --38.2%). ¶ Step ii)--.

COLUMN 60

Line 13, "50.6%). Step iii)" should read --50.6%). ¶ Step iii)--.

COLUMN 69

Line 13, "result" should read --results--.

UNITED STATES PATENT AND TRADEMARK OFFICE
CERTIFICATE OF CORRECTION

PATENT NO. : 5,188,762
DATED : February 23, 1993
INVENTOR(S) : TAKASHI IWAKI, ET AL.

It is certified that error appears in the above-identified patent and that said Letters Patent is hereby corrected as shown below:

COLUMN 86

Line 27, "

| Composition | Response time (μsec) | |
|---|---|---|
| | 10° C | 20° C |
| R | 515 | 217 |
| S | 569 | 230 |

"

should read

-- 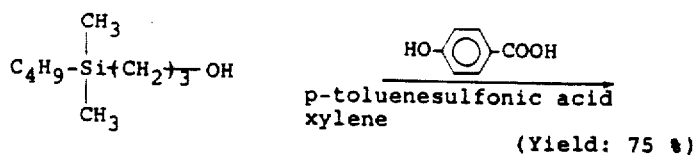

(Yield: 75 %)

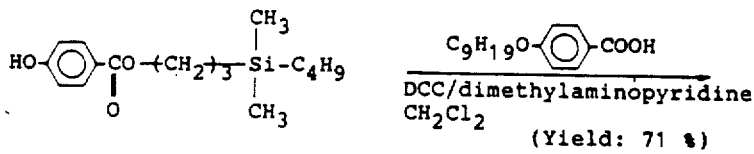

(Yield: 71 %)

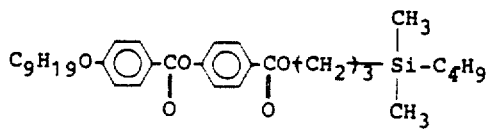

Phase transition temperature (°C)

$$\text{Cryst.} \xrightarrow[6]{21} \text{SmC} \xrightarrow[33]{33} \text{SmA} \xrightarrow[35]{37} \text{Iso.}$$

--.

UNITED STATES PATENT AND TRADEMARK OFFICE
CERTIFICATE OF CORRECTION

PATENT NO.  : 5,188,762
DATED       : February 23, 1993
INVENTOR(S) : TAKASHI IWAKI, ET AL.

Page 3 of 3

It is certified that error appears in the above-identified patent and that said Letters Patent is hereby corrected as shown below:

COLUMN 91

Line 28, "compound," should read --compounds,--.

Signed and Sealed this

Fifteenth Day of March, 1994

Attest:

BRUCE LEHMAN

Attesting Officer    Commissioner of Patents and Trademarks